United States Patent
Mack

(10) Patent No.: US 9,447,382 B2
(45) Date of Patent: *Sep. 20, 2016

(54) GENERATION OF INDUCED PLURIPOTENT STEM CELLS FROM SMALL VOLUMES OF PERIPHERAL BLOOD

(71) Applicant: Cellular Dynamics International, Inc., Madison, WI (US)

(72) Inventor: Amanda Mack, Madison, WI (US)

(73) Assignee: Cellular Dynamics International, Inc., Madison, WI (US)

( * ) Notice: Subject to any disclaimer, the term of this patent is extended or adjusted under 35 U.S.C. 154(b) by 44 days.

This patent is subject to a terminal disclaimer.

(21) Appl. No.: 14/179,547

(22) Filed: Feb. 12, 2014

(65) Prior Publication Data

US 2014/0234973 A1    Aug. 21, 2014

Related U.S. Application Data

(60) Provisional application No. 61/355,046, filed on Jun. 15, 2010, provisional application No. 61/388,949, filed on Oct. 10, 2010.

(51) Int. Cl.
  *C12N 5/074* (2010.01)
  *C12N 15/85* (2006.01)

(52) U.S. Cl.
  CPC ............ *C12N 5/0696* (2013.01); *C12N 15/85* (2013.01); *C12N 2501/115* (2013.01); *C12N 2501/15* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2501/608* (2013.01); *C12N 2501/727* (2013.01); *C12N 2506/11* (2013.01); *C12N 2510/00* (2013.01)

(58) Field of Classification Search
  CPC ................ C12N 15/85; C12N 5/0696; C12N 2501/115; C12N 2506/11; C12N 2501/604; C12N 2510/00; C12N 2501/727; C12N 2501/602; C12N 2501/606; C12N 2501/15; C12N 2501/603; C12N 2501/605; C12N 2501/608
  See application file for complete search history.

(56) References Cited

U.S. PATENT DOCUMENTS

| | | | |
|---|---|---|---|
| 5,478,838 A | 12/1995 | Arita et al. | 514/300 |
| 5,728,581 A | 3/1998 | Schwartz et al. | 435/385 |
| 7,781,214 B2 | 8/2010 | Smith et al. | 435/377 |
| 8,048,675 B1 | 11/2011 | Irion | 435/455 |
| 8,546,140 B2 | 10/2013 | Mack et al. | 435/455 |
| 8,691,574 B2 * | 4/2014 | Mack | 435/377 |
| 8,741,648 B2 * | 6/2014 | Rajesh et al. | 435/455 |
| 2003/0087919 A1 | 5/2003 | Nagarathnam et al. | 514/266.23 |
| 2003/0125344 A1 | 7/2003 | Nagarathnam et al. | 514/266.2 |
| 2003/0211603 A1 | 11/2003 | Earp et al. | 435/366 |
| 2004/0002507 A1 | 1/2004 | Nagarathnam et al. | 514/275 |
| 2004/0002508 A1 | 1/2004 | Nagarathnam et al. | 514/275 |
| 2004/0014755 A1 | 1/2004 | Nagarathnam et al. | 514/234.5 |
| 2005/0123902 A1 | 6/2005 | Meneses et al. | 435/5 |
| 2005/0192304 A1 | 9/2005 | Nagarathnam et al. | 514/275 |
| 2005/0209261 A1 | 9/2005 | Nagarathnam et al. | 514/275 |
| 2007/0116680 A1 | 5/2007 | Stegemann et al. | 424/93.7 |
| 2007/0238170 A1 | 10/2007 | Thomson et al. | 435/366 |
| 2010/0003757 A1 | 1/2010 | Mack et al. | 435/455 |
| 2010/0021998 A1 | 1/2010 | Sanyal et al. | 435/366 |
| 2010/0041054 A1 | 2/2010 | Mack | 435/320.1 |

FOREIGN PATENT DOCUMENTS

| | | |
|---|---|---|
| WO | WOv 95/03693 | 2/1995 |
| WO | WO 95/05843 | 3/1995 |
| WO | WO 95/08105 | 3/1995 |
| WO | WO 2007/033592 | 9/1997 |
| WO | WO 9733592 A1 * | 9/1997 |
| WO | WO 02/076976 | 10/2002 |
| WO | WO 03/059913 | 7/2003 |
| WO | WO 03/062225 | 7/2003 |
| WO | WO 03/062227 | 7/2003 |
| WO | WO 2004/039796 | 5/2004 |
| WO | WO 2007/113505 | 10/2007 |
| WO | WO 2009-148057 | 12/2009 |
| WO | WO 2010-013845 | 2/2010 |
| WO | WO 2010-048567 | 4/2010 |
| WO | WO 2010/141801 | 12/2010 |
| WO | WO 2011/032166 | 3/2011 |
| WO | WO 2011/143343 | 11/2011 |

OTHER PUBLICATIONS

"A guide to serum-free cell culture," Gibco®, pp. 1-11, 2003.
"RetroNectin®," accessed from http://www.takara-bio.com, pp. 1-10, on Apr. 4, 2013.
Aasen and Belmonte, "Isolation and cultivation of human keratinocytes from skin or plucked hair for the generation of induced pluripotent stem cells," *Nat. Protoc.*, 5(2):371-382, 2010.
Akkina et al., "High-efficiency gene transfer into CD34+ cells with a human immunodeficiency virus type 1-based retroviral vector pseudotyped with vesicular stomatitis virus envelope glycoprotein G,", *J. Virol.*, 70(4):2581-2585, 1996.
Bain et al., "The selectivity of protein kinase inhibitors: a further update," *Biochem. J.*, 408(3):297-315, 2007.
Bode et al. "The hitchhiking principle: Optimizing Episomal vectors for the use in gene therapy and biotechnology," *Gene Ther. Mol. Biol.*, 6:33-46, 2001.
Chou et al., "Efficient human iPS cell derivation by a non-integrating plasmid from blood cells with unique epigenetic and gene expression signatures," *Cell Research*, 21:518-529, 2011.
Christ et al., "Improved purification of hematopoietic stem cells based on their elevated aldehyde dehydrogenase activity," *Haematologica*, 92(9):1165-72, 2007.

(Continued)

*Primary Examiner* — Thaian N Ton
(74) *Attorney, Agent, or Firm* — Parker Highlander PLLC

(57) ABSTRACT

Methods and compositions relating to the production of induced pluripotent stem cells (iPS cells) are disclosed. For example, induced pluripotent stem cells may be generated from peripheral blood cells, such as human blood progenitor cells, using episomal reprogramming and feeder-free or xeno-free conditions. In certain embodiments, the invention provides novel methods for improving overall reprogramming efficiency with low number of blood progenitor cells.

14 Claims, 11 Drawing Sheets

(56) References Cited

OTHER PUBLICATIONS

Delaney et al., "Notch-mediated expansion of human cord blood progenitor cells capable of rapid myeloid reconstitution," *Nat. Med.*, 16(2):232-236, 2010.

Eliasson and Jonsson, "The hematopoietic stem cell niche: low in oxygen but a nice place to be," *J. Cell Physiol.*, 222(1):17-22, 2010.

Eminli et al., "Differentiation stage determines potential of hematopoietic cells for reprogramming into induced pluripotent stem cells," *Nature Genetics*, 41(9):968-976, 2009.

Extended European Search Report issued in European Application No. 11796290.2, mailed Nov. 13, 2013.

Fernandes et al., "A dermal niche for multipotent adult skin-derived precursor cells," *Nature Cell Biology*, 6:1082-1093, 2004. Supplementary Information, 5 pages.

Giorgetti et al., "Generation of induced pluripotent stem cells from human cord blood cells with only two factors: Oct4 and Sox2," *Nature Protocols*, 5(4):811-820, 2010.

Gonzalez, "Generation of mouse-induced pluripotent stem cells by transient expression of a single nonviral polycistronic vector," *PNAS*, 106(22):8918-8922, 2009.

Hess et al., "Functional characterization of highly purified human hematopoietic repopulating cells isolated according to aldehyde dehydrogenase activity," *Blood*, 104(6):1648-55, 2004.

Jia et al., "A nonviral minicircle vector for deriving human iPS cells," *Nature Protocols*, 7(3):197-201, 2010.

Kadaja-Saarepuu et al., "CD43 promotes cell growth and helps to evade FAS-mediated apoptosis in non-hematopoietic cancer cells lacking the tumor suppressors p53 or ARF," *Oncogene*, 27(12):1705-1715, 2008.

Keller et al., "In vitro differentiation of embryonic stem cells," *Curr. Opin. Cell Biol.*, 7(6):862-9, 1995.

Koller et al., "Effects of synergistic cytokine combinations, low oxygen, and irradiated stroma on the expansion of human cord blood progenitors," *Blood*, 80(2):403-411, 1992.

Kunisato et al., "Direct generation of induced pluripotent stem cells from human nonmobilized blood," *Stem Cells and Development*, 20(1):159-168, 2011.

Lin et al., "A chemical platform for improved induction of human iPSCs," *Nature Methods*, 6(11):805-808, 2009.

Loh et al., "Generation of induced pluripotent stem cells from human blood," *Blood*, 113(22):5476-5479, 2009.

Loh, "Generation of induced pluripotent stem cells from human blood," *Blood*, Supplemental Materials, 113(220):5476-5479, 2009.

Ludwig et al., "Derivation of human embryonic stem cells in defined conditions," *Nat. Biotechnol.*, 24(2):185-187, 2006.

Ludwig et al., "Feeder-independent culture of human embryonic stem cells," *Nat. Methods*, 3(8):637-46, 2006.

Mack et al., "Generation of induced pluripotent stem cells from CD34+ cells across blood drawn from multiple donors with non-integrating episomal vectors," *PLoS One*, 6(11) e27956, 2011.

Maherali and Hochedinger, "Guidelines and techniques for the generation of induced pluripotent stem cells," *Cell Stem Cell*, 3:595-605, 2008.

Mallon et al., "Toward xeno-free culture of human embryonic stem cells," *The International Journal of Biochemistry & Cell Biology*, 38:1063-1075, 2006.

Office Action issued in Australian Application No. 2011267849, mailed Jan. 28, 2014.

Office Action issued in Chinese Application No. 201180029389.7, mailed Oct. 22, 2013.

Office Action issued in U.S. Appl. No. 13/160,076, mailed Apr. 10, 2013.

PCT International Preliminary Report on Patentability issued in International application No. PCT/US2011/040323, dated Nov. 5, 2012.

PCT International Search Report and Written Opinion issued in International application No. PCT/US2011/040323, dated Feb. 29, 2012.

Rajala et al., A defined and xeno-free culture method enabling the establishment of clinical-grade human embryonic, induced pluripotent and adipose stem cells, *PloS One*, 5(4):e10246, 2010.

Rajesh et al., "Human lymphoblastoid B-cell lines reprogrammed to EBV-free induced pluripotent stem cells," *Blood*, 118(7): 1797-1800, 2011.

Rinehart et al., "Multicenter phase II study of the oral MEK inhibitor, CI-1040, in patients with advanced non-small-cell lung, breast, colon, and pancreatic cancer," *J Clinical Oncol.*, 22:4456-4462, 2004.

Rodriguez-Piza et al., "Reprogramming of human fibroblasts to induced pluripotent stem cells under xeno-free conditions," *Stem Cells*, 28:36-44, 2009.

Schaffer et al., "Gene structure and alternative splicing of glycogen synthase kinase 3 beta (GSK-3beta) in neural and non-neural tissues," *Gene*, 302(1-2):73-81, 2003.

Stadtfeld, "Induced pluripotent stem cells generated without viral integration," *Science*, 322:945-949, 2008.

Sun et al., "Feeder-free derivation of induced pluripotent stem cells from adult human adipose stem cells," *Proc. Natl. Acad. Sci. USA*, 106(37):15720-15725, 2009. Supporting Information, doi: 10.1073/pans.0908450106. 11 pages.

Takahashi et al., "Induction of pluripotent stem cells from adult human fibroblasts by defined factors," *Cell*, 131(5):861-872, 2007.

Takahashi et al., "Induction of pluripotent stem cells from mouse embryonic and adult fibroblast cultures by defined factors," *Cell*, 126(4):663-676, 2006.

Takenaka et al., "Effective generation of iPS cells from CD34+ cord blood cells by inhibition of p53," *Experimental Hematology*, 38:154-162, 2009.

U.S. Appl. No. 61/058,858 entitled "Methods for the Production of iPS Cells Using Non Viral Approach," by Amanda Mack, filed Jun. 24, 2008.

Vodyanik et al., "Leukosialin (CD43) defines hematopoietic progenitors in human embryonic stem cell differentiation cultures," *Blood*, 108(6):2095-105, 2006.

Watanabe et al., "Directed differentiation of telencephalic precursors from embryonic stem cells," *Nat. Neurosci.*, 8(3):288-96, 2005.

Wu et al., "Optimization of culture conditions to enchance transfection of human $CD34^+$ cells by electroporation," *bone Marrow Translplantation*, 27:1201-1209, 2001.

Ye et al., "Human-induced pluripotent stem cells from blood cells of healthy donors and patients with acquired blood disorders," *Blood*, 114(27):5473-5480, 2009.

Ying et al., "The ground state of embryonic stem cell self-renewal," *Nature*, 453:519-23, 2008.

Yoshida et al., "Hypoxia enhances the generation of induced pluripotent stem cells," *Cell Stem Cell*, 5(3):237-41, 2009.

Yu et al., "Efficient feeder-free episomal reprogramming with small molecules," *PLoS One*, 6(3) e17557, 2011.

Yu et al., "Human induced pluripotent stem cells free of vector and transgene sequences," *Science*, 324:797-801, 2009.

Yu et al., "Induced pluripotent stem cell lines derived from human somatic cells," *Science*, 318:1917-1920, 2007.

Yuan et al., "Langerhans cells derived from genetically modified human $CD34^+$ hemopoietic progenitors are more potent than peptide-pulsed Langerhans cells for inducing antigen-specific $CD8^+$ cytolytic T lymphocyte responses,"*J. of Immunology*, 174(2):758-766, 2005.

Zhou et al., "Generation of induced pluripotent stem cell using recombinant proteins," *Cell Stem Cell*, 4:1-4, 2009.

Office Action issued in Japanese Application No. 2013-515431, mailed Dec. 24, 2015, and English language translation thereof.

* cited by examiner

GENERATION OF INDUCED PLURIPOTENT STEM CELLS FROM SMALL VOLUMES OF PERIPHERAL BLOOD

This application is a continuation of U.S. application Ser. No. 13/160,076, filed Jun. 14, 2011, which claims priority to U.S. Provisional Application No. 61/355,046, filed on Jun. 15, 2010 and U.S. Provisional Application No. 61/388,949, filed on Oct. 1, 2010. The entire disclosures of each of the above referenced disclosures are specifically incorporated herein by reference in their entirety without disclaimer. This application is also related to U.S. Application No. 61/184,546 filed on Jun. 5, 2009, U.S. Application No. 61/240,116 filed on Sep. 4, 2009, and PCT application PCT/US10/37376 filed on Jun. 4, 2010, the entire disclosures of which are specifically incorporated herein by reference in their entirety without disclaimer.

BACKGROUND OF THE INVENTION

1. Field of the Invention

The present invention relates generally to the field of molecular biology and stem cells. More particularly, it concerns reprogramming of somatic cells, especially hematopoietic progenitor cells.

2. Description of Related Art

In general, stem cells are undifferentiated cells which can give rise to a succession of mature functional cells. For example, a hematopoietic stem cell may give rise to any of the different types of terminally differentiated blood cells. Embryonic stem (ES) cells are derived from the embryo and are pluripotent, thus possessing the capability of developing into any organ or tissue type or, at least potentially, into a complete embryo.

Induced pluripotent stem cells, commonly abbreviated as iPS cells or iPSCs, are a type of pluripotent stem cell artificially derived from a non-pluripotent cell, typically an adult somatic cell. Induced pluripotent stem cells are believed to be identical to natural pluripotent stem cells, such as embryonic stem cells in many respects, such as in terms of the expression of certain stem cell genes and proteins, chromatin methylation patterns, doubling time, embryoid body formation, teratoma formation, viable chimera formation, and potency and differentiability, but the full extent of their relation to natural pluripotent stem cells is still being assessed.

IPS cells were first produced in 2006 (Takahashi et al., 2006) from mouse cells and in 2007 from human cells (Takahashi et al., 2007; Yu et al, 2007). This has been cited as an important advancement in stem cell research, as it may allow researchers to obtain pluripotent stem cells, which are important in research and potentially have therapeutic uses, without the controversial use of embryos.

In humans, iPS cells are commonly generated from dermal fibroblasts. However, the requirement for skin biopsies and the need to expand fibroblast cells for several passages in vitro make it a cumbersome source for generating patient-specific stem cells. Moreover, previous methods for reprogramming of human somatic cells are inconvenient because they need to obtain somatic cells directly from a human subject, or maintain the cells in a labor-intensive cell culture system.

Therefore, there is a need to develop methods to induce pluripotent stem cells from alternative sources which are simple, convenient, and easily accessible. In developing the present invention, the inventor considered that blood cells may be such a source because blood may be collected from a patient or a healthy individual, stored or transferred, for example, from a central unit for distribution to one or more remote places. However, there remains a need to develop more efficient methods for reprogramming blood cells, especially peripheral blood cells.

SUMMARY OF THE INVENTION

Aspects of the present invention are intended to increase the overall process efficiency (the conversion efficiency of input number of blood cells to output number of iPS lines) of reprogramming peripheral blood cells and decrease the volume of input blood volume needed to obtain a reasonable number of iPS colonies (for example, at least 5), for example, from a standard blood sample (in a volume of about 8-10 ml). Certain embodiments of the invention are novel by using the ability to expand the number of $CD34^+$ starting cells from peripheral blood to overcome the limitation on the small number of $CD34^+$ starting cells that one can get from non-mobilized peripheral blood. One person skilled in the art might have thought that expanding the $CD34^+$ cells, which inherently causes them also to differentiate, might make the cells less susceptible to reprogramming. The Examples of this invention demonstrated that the expanded cells provide a sufficient number for reprogramming and achieve an unexpectedly good overall process efficiency, much higher than the essentially identical condition without expansion. With this advance, certain aspects of the invention enable generating iPS cells from a small volume of peripheral blood, particularly from non-mobilized subjects.

On the other hand, certain aspects of the invention have the advantage of generating iPS cells from peripheral blood cells on a defined extracellular matrix to avoid the problems and potential xenogeneic contamination from undefined feeder cells. In a further aspect, the present invention also overcome the problem of using integrating vectors for reprogramming.

Accordingly, in a first embodiment there is provided a method for producing human iPS cells from hematopoietic progenitor cells, the method comprising one or more of the steps of: a) providing a cell population of human peripheral blood cells comprising hematopoietic progenitor cells; b) culturing the population under conditions to promote the expansion of the hematopoietic progenitor cells; c) introducing exogenous episomal genetic elements or exogenous RNA genetic elements that express iPS reprogramming factors into the expanded hematopoietic progenitor cells; and d) culturing the episomal-containing expanded hematopoietic progenitor cells in a culture essentially free of feeder cells or a feeder cell-conditioned medium, or in a xeno-free culture, thereby producing human iPS cells from the hematopoietic progenitor cells. In a particular aspect, the iPS cells may be produced from a small volume blood sample, for example, up to 10 ml with one or more steps described above. The expansion step may not always be necessary, but greatly increases reprogramming efficiency in an unexpected manner, particularly in the context of small blood volumes.

In certain aspects, the source of the cell population is from one or more subjects whose cells have not been mobilized with extrinsically applied granulocyte colony-stimulating factor (G-CSF) or granulocyte macrophage colony-stimulating factor (GM-CSF). The source of the cell population may be a blood sample or blood components. The suitable volume of a blood sample could be from about 1 to about 5 ml, about 1 to 10 ml, about 1 to 15 ml, or more specifically, about 1, 2, 3, 4, 5, 6, 7, 8, 9, 10, 11, 12, 13, 14, 15, 16, 17, 18, 19, 20, 25, 30, 40, 50 ml or any range derivable therein. The cell population may be obtained from a cryopreserved blood sample or the source of cell population or the cell population may have been cryopreserved.

For example, the cell population may comprise at least, about, or at most, $1 \times 10^3$, $2 \times 10^3$, $3 \times 10^3$, $4 \times 10^3$, $5 \times 10^3$, $6 \times 10^3$, $7 \times 10^3$, $8 \times 10^3$, $9 \times 10^3$, $1 \times 10^4$, $2 \times 10^4$, $3 \times 10^4$, $4 \times 10^4$, $5 \times 10^4$, $6 \times 10^4$, $7 \times 10^4$, $8 \times 10^4$, $9 \times 10^4$, $1 \times 10^5$, $2 \times 10^5$, $3 \times 10^5$, $4 \times 10^5$, $5 \times 10^5$, $6 \times 10^5$, $7 \times 10^5$, $8 \times 10^5$, $9 \times 10^5$, $1 \times 10^6$, $2 \times 10^6$ hematopoietic progenitor cells or any range derivable therein. In certain aspects, starting cells prior to expansion or reprogramming may comprise at least or about $10^3$, $10^4$, $10^5$, $10^6$, $10^7$, $10^8$, $10^9$, $10^{10}$, $10^{11}$, $10^{12}$, $10^{13}$ cells or any range derivable therein. The starting cell population may have a seeding density of at least or about 10, $10^1$, $10^2$, $10^3$, $10^4$, $10^5$, $10^6$, $10^7$, $10^8$ cells/ml, or any range derivable therein. A standard blood sample of 8 to 10 ml may have 6-12,000 $CD34^+$ cells and normally will not be sufficient for reprogramming to yield iPS cell colonies. However, some aspects of the present invention provide methods for expanding progenitor cells to a sufficient number and reprogramming expanded cells to achieve successful production of iPS cells. In a particular aspect, the cell population may be essentially free of any terminally differentiated blood cells, like T cells or B cells, therefore the iPS cells derived therefrom may have a complete genome without genetic rearrangements.

Any method useful for isolating the hematopoietic progenitor cells may be employed in step a) of the present method. For example, such isolation may be based on surface marker expression, which may comprise positive selection of CD34 expression and/or negative selection of lineage-specific marker expression. The selection methods may include Magnetic-activated cell sorting (MACS®) or Fluorescence Activated Cell Sorting (FACS™, i.e., flow cytometry).

For expansion of hematopoietic progenitor cells or culturing of reprogrammed hematopoietic progenitor cells at an initial recovery stage, the cells may be cultured under conditions that comprise an expansion medium comprising one or more cytokines including stem cell factor (SCF), Flt-3 ligand (Flt3L), thrombopoietin (TPO), Interleukin 3 (IL-3), or Interleukin 6 (IL-6). The expansion condition may further comprise a Notch-1 ligand, such as an immobilized engineered Notch ligand (Deltalext-IgG; Delaney et al., 2010), or may not comprise such a Notch-1 ligand as it is demonstrated to be peripheral for the purpose. The cell may be expanded for about 1, 2, 3, 4, 5, 6, 7, 8, 9, 10, 11, 12, 13, 14, 15, 16, 17, 18, 19, 20, 21, 22, 23, 24, 25 days or any range derivable therein prior to the reprogramming step. For example, the reprogramming elements may be introduced into cells at about days 3, 4, 5, or 6 of the expansion phase.

The expansion condition for hematopoietic progenitor cells may be essentially free of any matrix components or, alternatively, may include a defined or xeno-free extracellular matrix, such as a human fibronectin fragment, like Retronectin®.

To facilitate in vitro expansion of hematopoietic progenitor cells by mimicking their in vivo microenvironment, the condition for expansion of hematopoietic progenitor cells or culturing of reprogrammed hematopoietic progenitor cells at an initial recovery stage may be a low oxygen condition, for example, from about 1 to 7% oxygen tension, particularly, about 2-5% oxygen.

In still further aspects of the invention, any method may be used for introducing the exogenous genetic elements to the cells, such as electroporation or lipid-mediated gene delivery.

In certain aspects, the episomal genetic elements may comprise a replication origin and one or more expression cassettes for expression of reprogramming factors. Such one or more of the expression cassettes may further comprise a nucleotide sequence encoding a trans-acting factor that binds to the replication origin to replicate an extra-chromosomal template. Alternatively, the peripheral blood cells may express such a trans-acting factor.

In exemplary embodiments, the replication origin may be a replication origin of a lymphotrophic herpes virus or a gamma herpes virus, an adenovirus, SV40, a bovine papilloma virus, or a yeast, such as a replication origin of a lymphotrophic herpes virus or a gamma herpes virus corresponding to oriP of EBV. In a further aspect, the lymphotrophic herpes virus may be Epstein Barr virus (EBV), Kaposi's sarcoma herpes virus (KSHV), Herpes virus saimiri (HS), or Marek's disease virus (MDV).

For replication and transient maintenance of exogenous episomal genetic elements, the trans-acting factor may be a polypeptide corresponding to, or a derivative of, a wild-type protein of EBNA-1 (EBV nuclear antigen 1) of EBV, preferably in the presence of a replication origin corresponding to OriP of EBV. The derivative may have a reduced ability to activate transcription from an integrated template as compared to wild-type EBNA-1 and thus reduced chances to ectopically activate chromosome genes to cause oncogenic transformation. Meanwhile, the derivative may activate transcription at least 5% of the corresponding wild-type protein from an extra-chromosomal template after the derivative binds the replication origin.

For reprogramming of hematopoietic progenitor cells, certain aspects of the present methods may involve using the reprogramming factors that may comprise one or more selected from the group consisting of Sox, Oct, Nanog, Lin-28, Klf4, and either C-myc or L-myc, or a combination thereof, for example, a set of Sox, Oct, Nanog, and optionally Lin-28, a set of Sox, Oct, Klf4, and optionally C-myc or L-myc, or a combination of these six factors. In certain aspects, to reduce the possible toxic effect of C-myc expression, the SV40 large T gene (SV40LT) may be included with C-myc. In particular aspects, the exogenous elements, either DNA or RNA, may comprise one or more polycistronic cassettes, such as two or more reprogramming factor genes under the same transcriptional regulatory element.

In some further aspects, hematopoietic progenitor cells which have been introduced with exogenous reprogramming factors may be cultured in the presence of a xeno-free extracellular matrix. For human cells, the xeno-free matrix is defined as an extracellular matrix essentially free of animal components, wherein the animal is not a human. In a particular aspect, the matrix may be defined, for example, having a single type of extracellular matrix peptide, such as a human fibronectin fragment, e.g., Retronectin®.

Furthermore, the step d) after introduction of exogenous genetic elements for reprogramming, the cells may be cultured under more than one distinct conditions. In the first sub-step immediately after the introduction of reprogramming elements, the cells may be cultured in a hematopoietic progenitor cell expansion medium as described above, or a reprogramming medium, a combination or equivalent thereof. For example, the cells may be cultured under a condition comprising a medium comprising one or more cytokines including stem cell factor (SCF), Flt-3 ligand (Flt3L), thrombopoietin (TPO), Interleukin 3 (IL-3), or Interleukin 6 (IL-6) for recovery of hematopoietic progenitor cells. This sub-step may last about, at least, or at most 2, 4, 8, 12, 16, 24, 32, 48, 96 hours or any range derivable therein. In this sub-step, a matrix component may be optional. After this sub-step, the cells may be transferred to a matrix, if not already on one.

The cells may be further cultured under a condition comprising an expansion medium; a reprogramming medium, such as a medium comprising a GSK-3 inhibitor, a MEK inhibitor, a TGF-β receptor inhibitor, a myosin II ATPase inhibitor, and/or a Rho-associated kinase (ROCK) signaling inhibitor to enhance reprogramming efficiently; a combination thereof or equivalent thereof followed by transition to 100% reprogramming medium. For example, the GSK-3 inhibitor may be CHIR99021; the MEK inhibitor may be PD0325901; the TGF-β receptor inhibitor may be A-83-01; the myosin II ATPase inhibitor may be blebbistatin; the ROCK inhibitor may be HA-100 or H1152. This sub-step may last about, at least, or at most, 1, 2, 3, 4, 5, 6, 7, 8, 9, 10, 11, 12, 13, 14, 15, 16, 17, 18, 19, 20 days or any range derivable therein. In some aspects, the reprogramming medium may be chemically defined, or may be based on TeSR medium, human embryonic cell culture medium, or N2B27 medium. In a further aspect, the cells may be transferred, preferably gradually, to a medium essentially free of extrinsically applied signaling inhibitors, such as a GSK-3 inhibitor, a MEK inhibitor, myosin II ATPase inhibitor, and a TGF-β receptor inhibitor. Such a medium may be TeSR2 or other stem cell medium and may be preferably chemically defined.

Any medium, culture or matrix for any of the steps or sub-steps or throughout the whole process may be xeno-free or defined. A medium may be chemically defined, such as TeSR™ medium.

In certain aspects, the methods may further comprise selecting the iPS cells, for example, based on one or more embryonic cell characteristics, such as an ES cell-like morphology. In a further aspect, the methods may comprise culturing the selected iPS cells in a iPS cell expansion medium comprising one or more selected from the group consisting of a GSK-3 inhibitor, a MEK inhibitor, a myosin II ATPase inhibitor, a TGF-β receptor inhibitor, a Rho-associated kinase (ROCK) signaling inhibitor, optionally leukemia inhibitory factor (LIF), or a combination thereof.

A population of iPS cells produced according to the above methods may also be provided.

There may also be provided a cell culture composition comprising a cell population of human peripheral blood cells comprising hematopoietic progenitor cells and progeny cells thereof, a xeno-free extracellular matrix, and a medium, wherein the hematopoietic progenitor cells comprise one or more exogenous episomal or RNA genetic elements that express reprogramming factors. Particularly, the matrix may be defined. For example, the matrix may have a single type of extracellular matrix peptide, such as a recombinant fibronectin fragment. The recombinant fibronectin fragment may be RetroNectin®. In further aspects, the cell culture composition may be xeno-free or defined. The medium comprised in the culture composition may be xeno-free or chemically defined. Such a medium may comprise one or more cytokines including stem cell factor (SCF), Flt-3 ligand (Flt3L), thrombopoietin (TPO), Interleukin 3 (IL-3), or Interleukin 6 (IL-6) for an initial stage of reprogrammed hematopoietic progenitor cells. This culture composition may also comprise a Notch-1 ligand, such as an immobilized engineered Notch ligand (Deltalext-IgG; Delaney et al., 2010). For enhancing reprogramming efficiency, the medium may comprise a GSK-3 inhibitor, a MEK inhibitor, a TGF-β receptor inhibitor, a myosin II ATPase inhibitor, and/or a Rho-associated kinase (ROCK) signaling inhibitor.

In the cell culture composition, the cell population of human peripheral blood cells may be from one or more subjects whose cells have not been mobilized with extrinsically applied granulocyte colony-stimulating factor (G-CSF) or granulocyte macrophage colony-stimulating factor (GM-CSF). The hematopoietic progenitor cells may have been expanded in vitro, for example, in the presence of one or more cytokines including stem cell factor (SCF), Flt-3 ligand (Flt3L), thrombopoietin (TPO), Interleukin 3 (IL-3), or Interleukin 6 (IL-6). The expansion culture may be a suspension cell culture and may not need use any substrate or matrix as described above. The source of the cell population may be a blood sample or blood components. The suitable volume of a blood sample could be from about 1 to about 5 ml, about 1 to 10 ml, about 1 to 15 ml, or more specifically, about 3, 4, 5, 6, 7, 8, 9, 10 ml or any range derivable therein. The cell population may be obtained from a cryopreserved blood sample or the source of cell population or the cell population may have been cryopreserved.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan; however, these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A demonstrates expansion of HPs from a single, non-mobilized blood donor using three testing conditions. Each condition relied on the cytokine-enriched medium while matrices varied from matrix-free, fibronectin-coated (Notch−), and fibronectin/DLL-1 coated (Notch+). FIG. 2B shows the natural decline in CD34 expression that occurs as progenitors drift toward more differentiated cell types. CD45 expression is an indicator of hematopoietic cells in general. Cells from the same donor sampled at 10 days during expansion exhibited an expression profile that was predominately myeloid in nature (FIG. 2C) with very little to no expression of B, T, and NK markers (data not shown). Furthermore, it was found herein that the expansion is consistent across multiple donors but the magnitude of that expansion varies among patient samples (FIG. 2D). A pool of 5 donors was created to establish a larger number of cells for multiple reprogramming experiments to be performed. The expansion potential for this pool was determined twice (Replicates 1 and 2, R1 and R2) (FIG. 2E).

FIG. 5A. Purified cells from PBMCs derived from donor GG (leukopak source) were expanded for 6 days. A range of cell numbers were transfected with a control, oriP/EBNA1-based plasmid expressing GFP. Transfection efficiency was determined by calculating the percentage of viable cells expressing GFP detected by flow cytometry. FIG. 5B. Purified cells from PBMCs (donor A2389) were expanded for 3 or 6 days and $6\times10^4$ to $1\times10^5$ cells were transfected with the control, GFP-expressing plasmid. The graph depicts the percent of the total population that is GFP-positive and the absolute number of total cells. FIG. 5C. This graph represents the fraction of cells in b that also co-express GFP and CD34 when transfected at 3 or 6 days of expansion. FIG. 5D. Representative reprogramming trial from freshly drawn blood (donor 3002) using combination plasmid set 2 for transfection. A single well is shown from a 6 well plate that contains colonies staining positively for alkaline phosphatase activity (i). The white arrowhead highlights the colony magnified in panel ii that also stained positively for Tra1-81 expression, panel iii. FIG. 5E. Reprogramming trials were performed using plasmid Set 2 on a range of input cell numbers expanded for 6 days (donor GG). FIG. 5F. CD34-expressing cells purified from four different donors were expanded for 6 days and transfected using the plasmid combination that expresses C-myc (Set 1) or L-myc (Set 2) to compare and the total number of iPSCs were compared.

FIG. 7A. Representative reprogramming trial whereby both the CD34 positive (i) and negative (ii) fractions following purification were used for reprogramming. Panel (i) shows one well of a 6 well plate that contains successfully reprogrammed colonies from donor 2939 based on their ability to express Alkaline Phosphatase (AP stain, blue). The CD34-depleted fraction from donor 2939 was unable to form colonies as indicated by the lack of AP staining when performed in parallel with the purified population panel, ii. Panels iii and iv magnify the colony in panel (i) marked by a white arrowhead and demonstrate expression of Tra1-81 (green). FIG. 7B. Cells purified from four different blood donors were expanded for 3, 6, 9, or 13 days. A population of cells from all or a subset of time points were tested in the feeder-free reprogramming protocol using the L-myc expressing plasmid DNA combination set 2. The efficiency of reprogramming was calculated as the total number of iPSCs exhibiting morphological features characteristic of an ES cell and an ability to stain positively for Tra1-81 divided by the total number of cells used for transfection. Black Squares depict the percentage of the population expressing CD34 at the indicated time points.

FIG. 8A. Fold expansion of CD34-expressing cells pooled from multiple donors in standard (n=13) and completely defined, animal-free media (n=2) after 6 days of expansion. Fold expansion was calculated from the total number of cells at day 6 divided by the number of cells the day after purification. Percentages indicate the fraction of cells expressing CD34 in the total population. FIG. 8B. The image represents one well of a 6 well plate containing colonies that stained positively for alkalkine phosphatase following reprogramming of expanded cells enriched for CD34-expression with fully defined, animal-free reagents.

DESCRIPTION OF ILLUSTRATIVE EMBODIMENTS

I. Introduction

Figure 1:
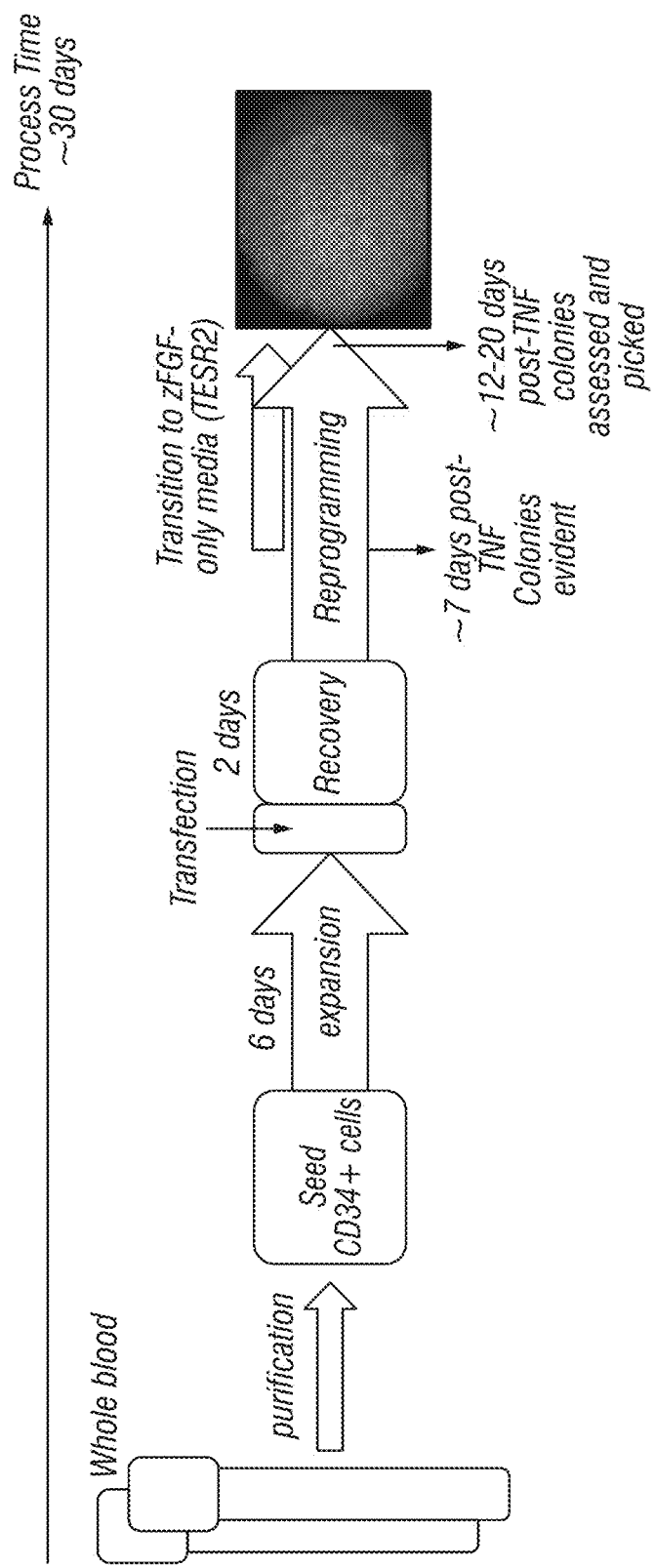
FIG. 1—Schematic of an exemplary reprogramming process. In a standard manner, 8 ml vials of whole blood are processed to obtain PBMCs, which are either frozen or purified fresh to enrich for CD34-expressing cells. These cells are then seeded for an expansion period to obtain an optimal number of cells for transfection. The transfected cells are then resuspended in 100% fresh expansion media or in combination with the reprogramming media complexed with small molecules. Within at least 48 hours, cells are transitioned to a defined, feeder free matrix and fed every other day with 100% reprogramming media complexed with small molecules. At approximately 9 to 14 days post-transfection (dpt), the culture is fed with a defined pluripotent stem cell media free of small molecules (i.e. TeSR2). Colonies are then stained by 18-25 dpt with Tra1-81 to identify iPS colonies.

The invention relates to methods and compositions for improving the overall process efficiency of reprogramming of peripheral blood cells. Such reprogramming may be under xeno-free or defined conditions and may be essentially free of exogenous retroviral genetic elements, therefore making more clinically relevant iPS cells.

Thorough assessment of the clinical relevance of iPS cells has been hampered by their derivation using ill-defined systems and methods involving viral-based methods that rely on chromosomal integration. For example, mouse embryonic fibroblasts (MEFs) have frequently been used as a support layer to facilitate iPS development along with reprogramming medium that has been conditioned in the presence MEFs. The inventor has found the efficiency of reprogramming is affected, in part, by the quality of the MEFs used which can vary between batches. It is therefore difficult to control and quantify that variability since the contribution MEFs impart on reprogramming is ill-defined. Therefore, it is preferable to establish a more defined system independent of MEFs that is amenable to manipulation so the outcome is more predictable. Multiple labs have succeeded in generating iPS cells using feeder-free substrates such as Matrigel™ (mouse origin) or derivatives thereof (Aasen and Belmonte, 2010; Sun et al., 2009), but none of them used peripheral blood cells or a xeno-free matrix.

Furthermore, viral-based methods of reprogramming have, to date, proven to be more efficient than non-integrating methods and therefore used more consistently to generate iPS cells. Unfortunately, the presence of integrated DNA carrying expression cassettes encoding known oncogenes such as C-myc and T-antigen are unacceptable for at least two reasons. Their presence always poses the threat of reactivation and expression of those genes that cannot be tolerated within the restricted criteria of clinical applications. The integration incurred by viral-based methods also occurs at multiple and often unpredictable locations that may disrupt the expression of endogenous genes present within the host DNA that may be crucial for controlling proliferation or critical cellular processes leading to variability in the performance of these cells in downstream analyses. Therefore a non-integrating strategy to generate iPS cells using defined conditions would alleviate this potential variability.

To provide patient specific cells to meet the demanding criteria for clinical application, iPS clones must be generated from tractable source material containing a high fraction of target cells or at least amenable to expansion, generated from feeder-free conditions, or chemically defined conditions, and reprogrammable via a process scalable across hundreds of samples. Blood is an extremely accessible tissue source routinely extracted from patients worldwide, and cells from mobilized and non-mobilized blood donors have been successfully reprogrammed by integrating viral vectors (Loh et al., 2009; Ye et al., 2009) (PloS, in press). Cells enriched for CD34 expression, in particular, have been shown to reprogram more efficiently than fibroblasts.

However, the current methods to reprogram CD34$^+$ cells do not satisfy the rigorous, xeno-free criteria necessary for clinical applications. First, CD34$^+$ cells constitute only a small fraction (0.1%) of non-mobilized peripheral blood (only 1000 cells per ml of blood). Secondly, investigators have relied on viral-based methods that require integration into the chromosomal DNA. Thirdly, the published methods involve MEFs and conditioned medium and, therefore, are ill-defined and contain xenogeneic contamination.

This invention is based, in part, on the discovery of a fully defined process to generate iPS cells from peripheral blood. As shown in the Examples, there is provided a method to expand the population of CD34 expressing cells from less than 10 ml of blood and to generate iPS cells under feeder-free conditions free from integrated and eventually extrachromosomal DNA.

Further embodiments and advantages of the invention are described below.

II. Definitions

"Reprogramming" is a process that confers on a cell a measurably increased capacity to form progeny of at least one new cell type, either in culture or in vivo, than it would have under the same conditions without reprogramming. More specifically, reprogramming is a process that confers on a somatic cell a pluripotent potential. This means that after sufficient proliferation, a measurable proportion of progeny having phenotypic characteristics of the new cell type if essentially no such progeny could form before reprogramming; otherwise, the proportion having characteristics of the new cell type is measurably more than before reprogramming. Under certain conditions, the proportion of progeny with characteristics of the new cell type may be at least about 1%, 5%, 25% or more in the in order of increasing preference.

The term "xeno-free (XF)" or "animal component-free (ACF)" or "animal free," when used in relation to a medium, an extracellular matrix, or a culture condition, refers to a medium, an extracellular matrix, or a culture condition which is essentially free from heterogeneous animal-derived components. For culturing human cells, any proteins of a non-human animal, such as mouse, would be xeno components. In certain aspects, the xeno-free matrix may be essentially free of any non-human animal-derived components, therefore excluding mouse feeder cells or Matrigel™. Matrigel™ is a solubilized basement membrane preparation extracted from the Engelbreth-Holm-Swarm (EHS) mouse sarcoma, a tumor rich in extracellular matrix proteins to include laminin (a major component), collagen IV, heparan sulfate proteoglycans, and entactin/nidogen.

The term "defined," when used in relation to a medium, an extracellular matrix, or a culture condition, refers to a medium, an extracellular matrix, or a culture condition in which the nature and amounts of approximately all the components are known.

A "chemically defined medium" refers to a medium in which the chemical nature of approximately all the ingredients and their amounts are known. These media are also called synthetic media. Examples of chemically defined medium include TeSRT™.

Cells are "substantially free" of exogenous genetic elements or vector elements, as used herein, when they have less that 10% of the element(s), and are "essentially free" of exogenous genetic elements or vector elements when they have less than 1% of the element(s). However, even more desirable are cell populations wherein less than 0.5% or less than 0.1% of the total cell population comprise exogenous genetic elements or vector elements.

A culture, matrix or medium are "essentially free" of certain reagents, such as signaling inhibitors, animal components or feeder cells, when the culture, matrix or medium respectively have a level of these reagents lower than a detectable level using conventional detection methods known to a person of ordinary skill in the art or these agents have not been extrinsically added to the culture, matrix or medium.

"Peripheral blood cells" refer to the cellular components of blood, including red blood cells, white blood cells, and platelets, which are found within the circulating pool of blood.

"Hematopoietic progenitor cells" or "hematopoietic precursor cells" refers to cells which are committed to a hematopoietic lineage but are capable of further hematopoietic differentiation and include hematopoietic stem cells, multipotential hematopoietic stem cells (hematoblasts), myeloid progenitors, megakaryocyte progenitors, erythrocyte progenitors, and lymphoid progenitors. Hematopoietic stem cells (HSCs) are multipotent stem cells that give rise to all the blood cell types including myeloid (monocytes and macrophages, neutrophils, basophils, eosinophils, erythrocytes, megakaryocytes/platelets, dendritic cells), and lymphoid lineages (T-cells, B-cells, NK-cells). The hematopoietic progenitor cells may or may not express CD34. The hematopoietic progenitor cells may co-express CD133 and be negative for CD38 expression. In certain embodiments, certain human hematopoietic progenitor cells may not express CD34, but these cells may nonetheless be converted into iPS cells via the methods disclosed herein. Hematopoietic precursor cells include $CD34^+/CD45^+$ hematopoietic precursor cells and $CD34^+/CD45^+/CD43^+$ hematopoietic precursor cells. The $CD34^+/CD43^+/CD45^+$ hematopoietic precursor cells may be highly enriched for myeloid progenitors. Various lineages of hematopoietic progenitor cells, such as $CD34^+/CD43^+/CD45^+$ hematopoietic precursor cells, may be converted to iPS cells via the methods disclosed herein. Hematopoietic progenitor cells also include various subsets of primitive hematopoietic cells including: $CD34^-/CD133^+/CD38^-$ (primitive hematopoietic precursor cells), CD43(+)CD235a(+)CD41a(+/−) (erythro-megakaryopoietic), lin(−)CD34(+)CD43 (+)CD45(−) (multipotent), and lin(−) CD34(+)CD43(+)CD45 (+) (myeloid-skewed) cells, CD133+/ALDH+ (aldehydehehydrogenase) (e.g., Hess et al. 2004; Christ et al., 2007). It is anticipated that any of these primitive hematopoietic cell types or hematopoietic precursor cells may be converted into iPS cells as described herein.

A "vector" or "construct" (sometimes referred to as gene delivery or gene transfer "vehicle") refers to a macromolecule or complex of molecules comprising a polynucleotide to be delivered to a host cell, either in vitro or in vivo. A vector can be a linear or a circular molecule.

A "plasmid", a common type of a vector, is an extra-chromosomal DNA molecule separate from the chromosomal DNA which is capable of replicating independently of the chromosomal DNA. In certain cases, it is circular and double-stranded.

By "expression construct" or "expression cassette" is meant a nucleic acid molecule that is capable of directing transcription. An expression construct includes, at the least, a promoter or a structure functionally equivalent to a promoter. Additional elements, such as an enhancer, and/or a transcription termination signal, may also be included.

The term "exogenous," when used in relation to a protein, gene, nucleic acid, or polynucleotide in a cell or organism refers to a protein, gene, nucleic acid, or polynucleotide which has been introduced into the cell or organism by artificial means, or in relation a cell refers to a cell which was isolated and subsequently introduced to other cells or to an organism by artificial means. An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

A "gene," "polynucleotide," "coding region," "sequence," "segment," "fragment," or "transgene" which "encodes" a particular protein, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "cell" is herein used in its broadest sense in the art and refers to a living body which is a structural unit of tissue of a multicellular organism, is surrounded by a membrane structure which isolates it from the outside, has the capability of self replicating, and has genetic information and a mechanism for expressing it. Cells used herein may be naturally-occurring cells or artificially modified cells (e.g., fusion cells, genetically modified cells, etc.).

As used herein, the term "stem cell" refers to a cell capable of self replication and pluripotency. Typically, stem cells can regenerate an injured tissue. Stem cells herein may be, but are not limited to, embryonic stem (ES) cells or tissue stem cells (also called tissue-specific stem cell, or somatic stem cell). Any artificially produced cell which can have the above-described abilities (e.g., fusion cells, reprogrammed cells, or the like used herein) may be a stem cell.

"Embryonic stem (ES) cells" are pluripotent stem cells derived from early embryos. An ES cell was first established in 1981, which has also been applied to production of knockout mice since 1989. In 1998, a human ES cell was established, which is currently becoming available for regenerative medicine.

Unlike ES cells, tissue stem cells have a limited differentiation potential. Tissue stem cells are present at particular locations in tissues and have an undifferentiated intracellular structure. Therefore, the pluripotency of tissue stem cells is typically low. Tissue stem cells have a higher nucleus/cytoplasm ratio and have few intracellular organelles. Most tissue stem cells have low pluripotency, a long cell cycle, and proliferative ability beyond the life of the individual. Tissue stem cells are separated into categories, based on the sites from which the cells are derived, such as the dermal system, the digestive system, the bone marrow system, the nervous system, and the like. Tissue stem cells in the dermal system include epidermal stem cells, hair follicle stem cells, and the like. Tissue stem cells in the digestive system include pancreatic (common) stem cells, liver stem cells, and the like. Tissue stem cells in the bone marrow system include hematopoietic stem cells, mesenchymal stem cells, and the like. Tissue stem cells in the nervous system include neural stem cells, retinal stem cells, and the like.

"Induced pluripotent stem cells," commonly abbreviated as iPS cells or iPSCs, refer to a type of pluripotent stem cell artificially prepared from a non-pluripotent cell, typically an adult somatic cell, or terminally differentiated cell, such as fibroblast, a hematopoietic cell, a myocyte, a neuron, an epidermal cell, or the like, by introducing certain factors, referred to as reprogramming factors.

"Pluripotency" refers to a stem cell that has the potential to differentiate into all cells constituting one or more tissues or organs, or particularly, any of the three germ layers: endoderm (interior stomach lining, gastrointestinal tract, the lungs), mesoderm (muscle, bone, blood, urogenital), or ectoderm (epidermal tissues and nervous system). "Pluripotent stem cells" used herein refer to cells that can differentiate into cells derived from any of the three germ layers, for example, direct descendants of totipotent cells or induced pluripotent cells.

By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. The fusion polypeptide is particularly chimeric, i.e., composed of heterologous molecules.

III. Reprogramming of Blood Cells

To provide iPS cells from alternative sources in addition to dermal fibroblasts commonly used in the current art, methods for reprogramming a cell population comprising peripheral blood cells may be provided. It is also highly desirable to reprogram blood cells that are easily accessible and less exposed to environmental mutagens. For example, peripheral blood cells that are collected and stored in blood banks could be used as a source of either autologous or allogeneic but histocompatible iPS cell lines. More critically, the ability to reprogram blood cells is essential if one wishes to generate iPS cells containing somatic mutations that are restricted to the blood cells and found only in acquired hematologic disorders to investigate their pathogenesis. In certain embodiments, hematopoietic progenitor cells in the peripheral blood cell population are expanded to provide a significant number of starting cells for reprogramming. Therefore, reprogramming from human blood cells in the present invention represents a novel way of establishing iPS cells from donor cells that require little manipulation time in culture. The ability to reprogram cells from the human blood will facilitate the development of a reliable method to generate patient-specific stem cells.

A. Hematopoietic Progenitor Cells

Due to the significant medical potential of hematopoietic stem and progenitor cells, substantial work has been done to try to improve methods for the differentiation of hematopoietic progenitor cells from embryonic stem cells. In the human adult, hematopoietic stem cells present primarily in bone marrow produce heterogeneous populations of actively dividing hematopoietic (CD34$^+$) progenitor cells that differentiate into all the cells of the blood system. While it is anticipated that CD34$^+$ endothelial cells may be converted to iPS cells, in certain embodiments it may be desirable to use hematopoietic cells which are not endothelial cells; for example, in some instances it may be desirable to use hematopoietic progenitor cells or hematopoietic precursor cells which do not express CD31 or VE-cadherin. Other markers, such as the CD43 and/or CD45 marker, may also be used to help identify hematopoietic progenitor cells (e.g., Kadaja-Saarepuu et al., 2008; Vodyanik et al., 2006). Hematopoietic progenitor cells include various subsets of primitive hematopoietic cells including: CD43(+)CD235a (+)CD41a(+/−) (erythro-megakaryopoietic), lin(−)CD34(+) CD43 (+)CD45(−) (multipotent), and lin(−) CD34(+)CD43 (+)CD45(+) (myeloid-skewed) cells. In an adult human, hematopoietic progenitors proliferate and differentiate resulting in the generation of hundreds of billions of mature blood cells daily. Hematopoietic progenitor cells are also present in cord blood. In vitro, human embryonic stem cells may be differentiated into hematopoietic progenitor cells. Hematopoietic progenitor cells may also be expanded or enriched from a sample of peripheral blood as described below. The hematopoietic cells can be of human origin, murine origin or any other mammalian species.

Isolation of hematopoietic progenitor cells include any selection methods, including cell sorters, magnetic separation using antibody-coated magnetic beads, packed columns; affinity chromatography; cytotoxic agents joined to a monoclonal antibody or used in conjunction with a monoclonal antibody, including but not limited to, complement and cytotoxins; and "panning" with antibody attached to a solid matrix, e.g., plate, or any other convenient technique.

The use of separation or isolation techniques include, but are not limited to, those based on differences in physical (density gradient centrifugation and counter-flow centrifugal elutriation), cell surface (lectin and antibody affinity), and vital staining properties (mitochondria-binding dye rho123 and DNA-binding dye Hoechst 33342). Techniques providing accurate separation include but are not limited to, FACS (Fluorescence-activated cell sorting) or MACS (Magnetic-activated cell sorting), which can have varying degrees of sophistication, e.g., a plurality of color channels, low angle and obtuse light scattering detecting channels, impedance channels, etc.

The antibodies utilized in the preceding techniques or techniques used to assess cell type purity (such as flow cytometry) can be conjugated to identifiable agents including, but not limited to, enzymes, magnetic beads, colloidal magnetic beads, haptens, fluorochromes, metal compounds, radioactive compounds, drugs or haptens. The enzymes that can be conjugated to the antibodies include, but are not limited to, alkaline phosphatase, peroxidase, urease and β-galactosidase. The fluorochromes that can be conjugated to the antibodies include, but are not limited to, fluorescein isothiocyanate, tetramethylrhodamine isothiocyanate, phycoerythrin, allophycocyanins and Texas Red. For additional fluorochromes that can be conjugated to antibodies, see Haugland, Molecular Probes: Handbook of Fluorescent Probes and Research Chemicals (1992-1994). The metal compounds that can be conjugated to the antibodies include, but are not limited to, ferritin, colloidal gold, and particularly, colloidal superparamagnetic beads. The haptens that can be conjugated to the antibodies include, but are not limited to, biotin, digoxygenin, oxazalone, and nitrophenol. The radioactive compounds that can be conjugated or incorporated into the antibodies are known to the art, and include but are not limited to technetium $^{99}$m ($^{99}$TC), $^{125}$I and amino acids comprising any radionuclides, including, but not limited to, $^{14}$C, $^3$H and $^{35}$S.

Other techniques for positive selection may be employed, which permit accurate separation, such as affinity columns, and the like. The method should permit the removal to a residual amount of less than about 20%, preferably less than about 5%, of the non-target cell populations.

Cells may be selected based on light-scatter properties as well as their expression of various cell surface antigens. The purified stem cells have low side scatter and low to medium forward scatter profiles by FACS analysis. Cytospin preparations show the enriched stem cells to have a size between mature lymphoid cells and mature granulocytes.

It also is possible to enrich the inoculation population for $CD34^+$ cells prior to culture, using for example, the method of Sutherland et al. (1992) and that described in U.S. Pat. No. 4,714,680. For example, the cells are subject to negative selection to remove those cells that express lineage specific markers. In an illustrative embodiment, a cell population may be subjected to negative selection for depletion of non-$CD34^+$ hematopoietic cells and/or particular hematopoietic cell subsets. Negative selection can be performed on the basis of cell surface expression of a variety of molecules, including T cell markers such as CD2, CD4 and CD8; B cell markers such as CD10, CD19 and CD20; monocyte marker CD14; the NK cell marker CD2, CD16, and CD56 or any lineage specific markers. Negative selection can be performed on the basis of cell surface expression of a variety of molecules, such as a cocktail of antibodies (e.g., CD2, CD3, CD11b, CD14, CD15, CD16, CD19, CD56, CD123, and CD235a) which may be used for separation of other cell types, e.g., via MACS or column separation.

As used herein, lineage-negative ($LIN^-$) refers to cells lacking at least one marker associated with lineage committed cells, e.g., markers associated with T cells (such as CD2, 3, 4 and 8), B cells (such as CD10, 19 and 20), myeloid cells (such as CD14, 15, 16 and 33), natural killer ("NK") cells (such as CD2, 16 and 56), RBC (such as glycophorin A), megakaryocytes (CD41), mast cells, eosinophils or basophils or other markers such as CD38, CD71, and HLA-DR. Preferably the lineage specific markers include, but are not limited to, at least one of CD2, CD14, CD15, CD16, CD19, CD20, CD33, CD38, HLA-DR and CD71. More preferably, $LIN^-$ will include at least CD14 and CD15. Further purification can be achieved by positive selection for, e.g., c-$kit^+$ or Thy-$1^+$. Further enrichment can be obtained by use of the mitochondrial binding dye rhodamine 123 and selection for rhodamine$^+$ cells, by methods known in the art. A highly enriched composition can be obtained by selective isolation of cells that are $CD34^+$, preferably $CD34^+LIN^-$, and most preferably, $CD34^+Thy-1^+LIN^-$. Populations highly enriched in stem cells and methods for obtaining them are well known to those of skill in the art, see e.g., methods described in PCT/US94/09760; PCT/US94/08574 and PCT/US94/10501.

Various techniques may be employed to separate the cells by initially removing cells of dedicated lineage. Monoclonal antibodies are particularly useful for identifying markers associated with particular cell lineages and/or stages of differentiation. The antibodies may be attached to a solid support to allow for crude separation. The separation techniques employed should maximize the retention of viability of the fraction to be collected. Various techniques of different efficacy may be employed to obtain "relatively crude" separations. Such separations are where up to 10%, usually not more than about 5%, preferably not more than about 1%, of the total cells present are undesired cells that remain with the cell population to be retained. The particular technique employed will depend upon efficiency of separation, associated cytotoxicity, ease and speed of performance, and necessity for sophisticated equipment and/or technical skill.

Selection of the hematopoietic progenitor cells need not be achieved solely with a marker specific for the cells. By using a combination of negative selection and positive selection, enriched cell populations can be obtained.

B. Sources of Blood Cells

Hematopoietic stem cells (HSCs) normally reside in the bone marrow but can be forced into the blood, a process termed mobilization used clinically to harvest large numbers of HSCs in peripheral blood. One mobilizing agent of choice is granulocyte colony-stimulating factor (G-CSF).

$CD34^+$ hematopoietic stem cells or progenitors that circulate in the peripheral blood can be collected by apheresis techniques either in the unperturbed state, or after mobilization following the external administration of hematopoietic growth factors like G-CSF. The number of the stem or progenitor cells collected following mobilization is greater than that obtained after apheresis in the unperturbed state. In a particular aspect of the present invention, the source of the cell population is a subject whose cells have not been mobilized by extrinsically applied factors because there is no need to enrich hematopoietic stem cells or progenitor cells in vivo.

Populations of cells for use in the methods described herein may be mammalian cells, such as human cells, non-human primate cells, rodent cells (e.g., mouse or rat), bovine cells, ovine cells, porcine cells, equine cells, sheep cell, canine cells, and feline cells or a mixture thereof. Non-human primate cells include rhesus macaque cells. The cells may be obtained from an animal, e.g., a human patient, or they may be from cell lines. If the cells are obtained from an animal, they may be used as such, e.g., as unseparated cells (i.e., a mixed population); they may have been established in culture first, e.g., by transformation; or they may have been subjected to preliminary purification methods. For example, a cell population may be manipulated by positive or negative selection based on expression of cell surface markers; stimulated with one or more antigens in vitro or in vivo; treated with one or more biological modifiers in vitro or in vivo; or a combination of any or all of these.

Populations of cells include peripheral blood mononuclear cells (PBMC), whole blood or fractions thereof containing mixed populations, spleen cells, bone marrow cells, tumor infiltrating lymphocytes, cells obtained by leukapheresis, biopsy tissue, lymph nodes, e.g., lymph nodes draining from a tumor. Suitable donors include immunized donors, non-immunized (naive) donors, treated or untreated donors. A "treated" donor is one that has been exposed to one or more biological modifiers. An "untreated" donor has not been exposed to one or more biological modifiers.

For example, peripheral blood mononuclear cells (PBMC) can be obtained as described according to methods known in the art. Examples of such methods are discussed by Kim et al. (1992); Biswas et al. (1990); Biswas et al. (1991).

Methods of obtaining hematopoietic precursor cells from populations of cells are also well known in the art. Hematopoietic precursor cells may be expanded using various cytokines, such as hSCF, hFLT3, and/or IL-3 (Akkina et al., 1996), or $CD34^+$ cells may be enriched using MACS or FACS. As mentioned above, negative selection techniques may also be used to enrich $CD34^+$ cells.

It is also possible to obtain a cell sample from a subject, and then to enrich it for a desired cell type. For example, PBMCs and/or $CD34^+$ hematopoietic cells can be isolated from blood as described herein. Cells can also be isolated from other cells using a variety of techniques, such as isolation and/or activation with an antibody binding to an epitope on the cell surface of the desired cell type. Another method that can be used includes negative selection using antibodies to cell surface markers to selectively enrich for a specific cell type without activating the cell by receptor engagement.

Bone marrow cells may be obtained from iliac crest, femora, tibiae, spine, rib or other medullary spaces. Bone marrow may be taken out of the patient and isolated through various separations and washing procedures. An exemplary procedure for isolation of bone marrow cells comprises the following steps: a) centrifugal separation of bone marrow suspension in three fractions and collecting the intermediate fraction, or buffycoat; b) the buffycoat fraction from step (a) is centrifuged one more time in a separation fluid, commonly Ficoll (a trademark of Pharmacia Fine Chemicals AB), and an intermediate fraction which contains the bone marrow cells is collected; and c) washing of the collected fraction from step (b) for recovery of re-transfusable bone marrow cells.

IV. Culture Conditions

Human pluripotent stem cells research is one of the most dynamic fields in modern biology. Human iPS cells, like human ES cells, have been mostly derived and cultured under a feeder layer of mouse embryonic fibroblasts (MEFs). For example, the therapeutical potential of human pluripotent stem cells lies in the transplantation of differentiated cell types for disorders such as Parkinson's disease and diabetes which arise from loss, or non-function, of a single cell type. However, these clinical applications are currently limited by xeno-contamination during the in vitro derivation and propagation phases. The mouse feeders or conditioned medium, as traditionally used, carry the risk of introducing non-human pathogens which would rule out transplantation in the future. Thus, bridging the gap between research models and clinical applications requires the design and implementation of xeno-free processes. Xeno-free (XF; or animal component-free, ACF; or animal free) culture condition, such as xeno-free media and xeno-free extracellular matrix, are therefore an essential element in the development of regenerative stem cell therapies, where implantation in humans is the desired. In addition, the efficiency of reprogramming may be impacted by the variability of MEF feeder cells used or any animal-derived products.

To improve the overall reprogramming efficiency from hematopoietic progenitor cells in peripheral blood and reduce the variability, there may be provided various feeder-free, xeno-free, or defined culture conditions, matrices or media for expansion of hematopoietic progenitor cells as well as reprogramming such cells.

A. Hematopoietic Progenitor Cell Expansion Condition

The expansion method of the invention may comprise inoculating the population of cells substantially enriched in hematopoietic progenitor cells and substantially free of stromal cells into an expansion container and in a volume of a suitable medium such that the cell density is from at least about 5,000, preferably 7,000 to about 200,000 cells/mL of medium, and more preferably from about 10,000 to about 150,000 cells/mL of medium, and at an initial oxygen concentration of from about 1 to 20% and preferably less than 8%. In one embodiment, the initial oxygen concentration is in a range from about 1, 2, 3, 4, 5, 6, 7%, or any range derivable therein.

In one aspect, the inoculating population of cells is derived from adult bone marrow and is from about 7,000 cells/mL to about 20,000 cells/mL and preferably about 20,000 cell/mL. In a separate aspect, the inoculation population of cells is derived from mobilized peripheral blood and is from about 20,000 cells/mL to about 50,000 cells/mL, preferably 50,000 cells/mL. In another aspect, the inoculating population of cells is derived from non-mobilized peripheral blood and is from about 7,000 cells/mL to about 50,000 cells/mL and preferably about 20,000 cell/mL.

Any suitable expansion container, flask, or appropriate tube such as a 24 well plate, 12.5 $cm^2$ T flask or gas-permeable bag can be used in the method of this invention. Such culture-containers are commercially available from Falcon, Corning or Costar. As used herein, "expansion container" also is intended to include any chamber or container for expanding cells whether or not free standing or incorporated into an expansion apparatus such as the bioreactors described herein. In one embodiment, the expansion container is a reduced volume space of the chamber which is formed by a depressed surface and a plane in which a remaining cell support surface is orientated.

Various media can be used for the expansion of the hematopoietic progenitor cells. Illustrative media include Dulbecco's MEM, IMDM and RPMI-1640 that can be supplemented with a variety of different nutrients, growth factors, cytokines, etc. The media can be serum free or supplemented with suitable amounts of serum such as fetal calf serum or autologous serum. Preferably, for being used in human therapy, the medium is serum-free or supplemented with autologous serum. One suitable medium is one containing IMDM, effective amounts of at least one of a peptone, a protease inhibitor and a pituitary extract and effective amounts of at least one of human serum albumin or plasma protein fraction, heparin, a reducing agent, insulin, transferrin and ethanolamine. In a further embodiment, the suitable expansion medium contains at least IMDM and 1-15% fetal bovine serum. Other suitable media formulations are well known to those of skill in the art, see for example, U.S. Pat. No. 5,728,581.

Regardless of the specific medium being used in any given hematopoietic progenitor cell expansion, the medium used is preferably supplemented with at least one cytokine at a concentration from about 0.1 ng/mL to about 500 ng mL, more usually 10 ng/mL to 100 ng/mL. Suitable cytokines, include but are not limited to, c-kit ligand (KL) (also called steel factor (StI), mast cell growth factor (MGF), and stem cell factor (SCF)), IL-6, G-CSF, IL-3, GM-CSF, IL-1α, IL-11 MIP-1α, LIF, c-mpl ligand/TPO, and flk2/flk3 ligand (Flt2L or Flt3L). (Nicola et al., 1979; Golde et al., 1980; Lusis, 1981; Abboud et al., 1981; Okabe, 1982; Fauser et al., 1981). Particularly, the culture will include at least one of SCF, Flt3L and TPO. More particularly, the culture will include SCF, Flt3L and TPO.

In one embodiment, the cytokines are contained in the media and replenished by media perfusion. Alternatively, when using a bioreactor system, the cytokines may be added separately, without media perfusion, as a concentrated solution through separate inlet ports. When cytokines are added without perfusion, they will typically be added as a 10× to 100× solution in an amount equal to one-tenth to $\frac{1}{100}$ of the volume in the bioreactors with fresh cytokines being added approximately every 2 to 4 days. Further, fresh concentrated cytokines also can be added separately in addition, to cytokines in the perfused media.

The cells may be then cultured under suitable conditions such that the cells condition the medium. Improved expansion of purified hematopoietic progenitor cells may be achieved when the culture medium is not changed, e.g., perfusion does not start until after the first several days of culture.

In certain aspects, suitable conditions comprise culturing at 33 to 39, and preferably around 37° C. (the initial oxygen concentration is preferably 4-8%, and most preferably, about 5%) for at least 6 days and preferably from about 7 to about 10 days, to allow release of autocrine factors from the cells without release of sufficient waste products to substantially inhibit hematopoietic progenitor cell expansion. After that time, the oxygen concentration may be increased to about 20%, either stepwise or gradually over the remainder of the culture period, which may be for a total of 10-28 days. Bone marrow stem cells, mobilized peripheral blood cells, or non-mobilized peripheral blood cells may be grown for around 1, 2, 3, 4, 5, 6, 7, 8, 9, 10, 11, 12, 13, 14, 15, 16, 17, 18, 19, 20, 21, 22, 23, 24, 25 days or any range derivable therein.

After the initial culture period without medium exchange, the culture medium may be exchanged at a rate which allows expansion of the hematopoietic progenitor cells. In a system where no variable volume is used, medium may be exchanged on day 7 (for mobilized peripheral blood stem cells) or on day 10 (for bone marrow cells). The exchange of fresh medium in a perfused system may be for example laminar. This uniform, nonturbulent, flow prevents the formation of "dead spaces" where patches of cells are not exposed to medium. The medium may be exchanged at a rate of from about 0.10/day to 0.50/day or $1/10$ to $1/2$ volume exchange per day. For example, the perfusion rate may be from about 0.25/day to 0.40/day. Most preferably, for bone marrow stem cells, perfusion may be at a rate of 0.27/day starting around day 14, and for mobilized or non-mobilized peripheral blood cells, perfusion starts at 0.25/day around day 10 and increases to 0.40/day around day 12.

Particularly, the cell concentration may be kept at an optimum throughout expansion. For instance, progenitor cells can expand up to ~1500 fold compared to a mononuclear cell (MNC) population which expands only ~10-20 fold. Progenitor cells have a large proliferative capacity, as such, where culture is performed in a closed system such a system must provide enough volume for total cell expansion. However, progenitor cells may also have a relatively high inoculation density. Optimal inoculation density and proliferation conditions can be achieved by growing the cells in a bioreactor such as the one described in U.S. Pat. No. 5,728,581. The cells may be seeded at the appropriate cell density in a depression and additional media are added when an appropriate cell density is attained. The shape of the device may allow the medium volume to be increased up to three-fold without significantly reducing the oxygen transfer efficiency to the cells.

B. Culture Conditions During and after Reprogramming

The starting cell (meaning, the expanded hematopoietic progenitor cell to be reprogrammed) and the end, reprogrammed cell generally have differing requirements for culture medium and conditions. To allow for this while also allowing reprogramming of the cell to occur, one or more transitional culture conditions may be needed. To initiate the reprogramming process, the expanded hematopoietic progenitor cells may be transfected at least, about or up to 0, 1, 2, 3, 4, 5, 6, 7, 8 or 9 days post seeding, more particularly 3, 4, 5, or 6 days post seeding and, in an exemplary embodiment, 6 days post seeding. In an alternate embodiment, the expansion step may not always be necessary. For example, if sufficient hematopoietic progenitor cells are obtained directly from purification from non-mobilized peripheral blood, reprogramming can be initiated without an expansion step. However, when dealing with a small volume of peripheral blood, for example, up to 10 ml in volume, an expansion step may be used to increase the numbers of hematopoietic progenitor cells and thus increase reprogramming efficiency.

Immediately after transfection and as a means to stabilize the cells after transfection, the cells may be cultured in a hematopoietic progenitor cell expansion medium as described above, or a medium comprising one or more cytokines and signaling inhibitors favoring the culture of reprogrammed cells, or a blend of the two types of conditions (equal or otherwise), all of which would optimally be xeno-free. Regardless of the medium utilized, the condition may be essentially free of any matrix components or it may comprise a matrix, which would preferably be a xeno-free matrix protein such as a fibronectin fragment. Such culture condition may be for a period of at least, about, or up to the first 0, 1, 2, 4, 6, 8, 10, 12, 24 hours or any range derivable therein post transfection. The cells could then be transitioned to a matrix, if not already on one, and cultured in a hematopoietic progenitor cell expansion medium as described above or a medium favoring reprogramming of cells or a blend of the two types of conditions (equal or otherwise), all of which would optimally be xeno-free. Regardless of the medium utilized, the cells would be gradually transitioned over one or two days with each medium refreshment to 100 percent reprogramming medium and such reprogramming condition may continue for a period of at least, about or up to 1, 2, 3, 4, 5, 6, 7, 8, 9, 10, 11, 12, 13, 14, 15 days following the transfection stabilization incubation.

After reprogramming factors are introduced into cells using the disclosed methods and cultured as described above, the resultant cells may be transferred to a medium sufficient to maintain the pluripotency of the cells, such as TeSR2. Such condition may preferably be obtained gradually during the latter half of the reprogramming condition by adding TeSR2 (or similar pluripotent cell culture medium) to the reprogramming medium without medium removal followed by complete replacement so that cells are cultured in 100% pluripotent cell culture medium. The culture of cells in pluripotent cell culture medium including the gradual transitional period may continue for a period of at least, about or up to 1, 2, 3, 4, 5, 6, 7, 8, 9, 10 days following the 100% reprogramming condition. This pluripotent cell culture condition may comprise an extracellular matrix because pluripotent stem cells are adherent cells.

Traditionally serum-containing medium on MEF feeders have been used. In certain aspects, the present invention obviates the need for serum or MEF feeder cells, and provides a defined process and condition for reprogramming cells.

Culturing of induced pluripotent stem (iPS) cells generated in this invention can use various medium and techniques developed to culture primate pluripotent stem cells, more specially, embryonic stem cells, as described in U.S. Pat. App. 20070238170 and U.S. Pat. App. 20030211603. It is appreciated that additional methods for the culture and maintenance of human pluripotent stem cells, as would be known to one of skill, may be used with the present invention.

Preferably, undefined conditions may not be used; for example, reprogrammed cells may not be cultured on fibroblast feeder cells or a medium which has been exposed to fibroblast feeder cells, especially mouse feeder cells. For example, pluripotent cells may be cultured and maintained in an essentially undifferentiated state using defined, feeder-independent culture system, such as a TeSR medium (Ludwig et al., 2006; Ludwig et al., 2006). Feeder-independent culture systems and media may be used to culture reprogrammed cells. These approaches allow reprogrammed cells to grow in an essentially undifferentiated state without the need for mouse fibroblast "feeder layers." As described herein, various modifications may be made to these methods in order to reduce costs as desired.

The medium according to certain aspects of the present invention can be prepared using a medium used for culturing animal cells as its basal medium, such as any of TeSR, BME, BGJb, CMRL 1066, Glasgow MEM, Improved MEM Zinc Option, IMDM, Medium 199, Eagle MEM, αMEM, DMEM, Ham, RPMI 1640, and Fischer's media, as well as any combinations thereof, but the medium is not particularly limited thereto as far as it can be used for culturing animal cells. Particularly, the medium may be xeno-free or chemically defined.

The medium according to the present invention can be a serum-containing or serum-free medium. The serum-free medium refers to media with no unprocessed or unpurified serum, and accordingly can include media with purified blood-derived components or animal tissue-derived components (such as growth factors). From the aspect of preventing contamination with heterogeneous animal-derived components, serum can be derived from the same animal as that of the stem cell(s).

The medium according to the present invention may contain or may not contain any alternatives to serum. The alternatives to serum can include materials which appropriately contain albumin (such as lipid-rich albumin, albumin substitutes such as recombinant albumin, plant starch, dextrans and protein hydrolysates), transferrin (or other iron transporters), fatty acids, insulin, collagen precursors, trace elements, 2-mercaptoethanol, 3'-thiolglycerol, or equivalents thereto. The alternatives to serum can be prepared by the method disclosed in International Publication No. 98/30679, for example. Alternatively, any commercially available materials can be used for more convenience. The commercially available materials include knockout Serum Replacement (KSR), Chemically-defined Lipid concentrated (Gibco), and Glutamax (Gibco).

The medium of the present invention can also contain fatty acids or lipids, amino acids (such as non-essential amino acids), vitamin(s), growth factors, cytokines, antioxidant substances, 2-mercaptoethanol, pyruvic acid, buffering agents, and inorganic salts. The concentration of 2-mercaptoethanol can be, for example, about 0.05 to 1.0 mM, and particularly about 0.1 to 0.5 mM, but the concentration is particularly not limited thereto as long as it is appropriate for culturing the stem cell(s).

A culture vessel used for culturing the cell(s) can include, but is particularly not limited to: flask, flask for tissue culture, dish, petri dish, dish for tissue culture, multi dish, micro plate, micro-well plate, multi plate, multi-well plate, micro slide, chamber slide, tube, tray, CellSTACK® Chambers, culture bag, and roller bottle, as long as it is capable of culturing the stem cells therein. The cells may be cultured in a volume of at least or about 0.2, 0.5, 1, 2, 5, 10, 20, 30, 40, 50 ml, 100 ml, 150 ml, 200 ml, 250 ml, 300 ml, 350 ml, 400 ml, 450 ml, 500 ml, 550 ml, 600 ml, 800 ml, 1000 ml, 1500 ml, or any range derivable therein, depending on the needs of the culture. In a certain embodiment, the culture vessel may be a bioreactor, which may refer to any device or system that supports a biologically active environment. The bioreactor may have a volume of at least or about 2, 4, 5, 6, 8, 10, 15, 20, 25, 50, 75, 100, 150, 200, 500 liters, 1, 2, 4, 6, 8, 10, 15 cubic meters, or any range derivable therein.

The culture vessel can be cellular adhesive or non-adhesive and selected depending on the purpose. The cellular adhesive culture vessel can be coated with any of substrates for cell adhesion such as extracellular matrix (ECM) to improve the adhesiveness of the vessel surface to the cells. The substrate for cell adhesion can be any material intended to attach cells. The substrate for cell adhesion includes collagen, gelatin, poly-L-lysine, poly-D-lysine, laminin, and fibronectin, fragments or mixtures thereof.

Other culturing conditions can be appropriately defined. For example, the culturing temperature can be about 30 to 40° C., for example, at least or about 31, 32, 33, 34, 35, 36, 37, 38, 39° C. but particularly not limited to them. The $CO_2$ concentration can be about 1 to 10%, for example, about 2 to 5%, or any range derivable therein. The oxygen tension can be at least, up to, or about 1, 2, 3, 4, 5, 6, 7, 8, 9, 10, 20%, or any range derivable therein.

The methods of the present invention can be also used for a suspension culture of cells such as reprogrammed cells or stem cells, including suspension culture on carriers (Fernandes et al., 2004) or gel/biopolymer encapsulation (United States Publication 2007/0116680). The term suspension culture of the cells means that the cells are cultured under non-adherent condition with respect to the culture vessel or feeder cells (if used) in a medium. The suspension culture of cells includes a dissociation culture of cells and an aggregate suspension culture of cells. The term dissociation culture of cells means that suspended stem cells is cultured, and the dissociation culture of stem cells include those of single cell or those of small cell aggregates composed of a plurality of cells (for example, about 2 to 400 cells). When the aforementioned dissociation culture is continued, the cultured, dissociated stem cells could form a larger aggregate of cells, and thereafter an aggregate suspension culture can be performed. The aggregate suspension culture includes an embryoid culture method (see Keller et al., 1995), and a SFEB method (Watanabe et al., 2005; International Publication No. 2005/123902).

C. Matrix Components

Various defined matrix components may be used in reprogramming peripheral blood cells to serve as a substrate for an adherent cell culture. For example, recombinant collagen IV, fibronectin, laminin, and vitronectin in combination may be used to coat a culturing surface as a means of providing a solid support for pluripotent cell growth, as described in Ludwig et al. (2006a; 2006b), which are incorporated by reference in its entirety.

A matrix composition may be immobilized on a surface to provide support for cells. The matrix composition may include one or more extracellular matrix (ECM) proteins and an aqueous solvent. The term "extracellular matrix" is recognized in the art. Its components include one or more of the following proteins: fibronectin, laminin, vitronectin, tenascin, entactin, thrombospondin, elastin, gelatin, collagen, fibrillin, merosin, anchorin, chondronectin, link protein, bone sialoprotein, osteocalcin, osteopontin, epinectin, hyaluronectin, undulin, epiligrin, and kalinin. Other extracellular matrix proteins are described in Kleinman et al., (1993), herein incorporated by reference. It is intended that the term "extracellular matrix" encompass a presently unknown extracellular matrix that may be discovered in the future, since its characterization as an extracellular matrix will be readily determinable by persons skilled in the art.

In some aspects, the total protein concentration in the matrix composition may be about 1 ng/mL to about 1 mg/mL. In some preferred embodiments, the total protein concentration in the matrix composition is about 1 μg/mL to about 300 µg/mL. In more preferred embodiments, the total protein concentration in the matrix composition is about 5 µg/mL to about 200 µg/mL.

The extracellular matrix (ECM) proteins may be of natural origin and purified from human or animal tissues. Alternatively, the ECM proteins may be genetically engineered recombinant proteins or synthetic in nature. The ECM proteins may be a whole protein or in the form of peptide fragments, native or engineered. Examples of ECM protein that may be useful in the matrix for cell culture include laminin, collagen I, collagen IV, fibronectin and vitronectin. In some embodiments, the matrix composition includes synthetically generated peptide fragments of fibronectin or recombinant fibronectin.

In still further embodiments, the matrix composition includes a mixture of at least fibronectin and vitronectin.

In some other embodiments, the matrix composition preferably includes laminin.

The matrix composition preferably includes a single type of extracellular matrix protein. In some preferred embodiments, the matrix composition includes fibronectin, particularly for use with culturing reprogrammed cells or hematopoietic progenitor cells. For example, a suitable matrix composition may be prepared by diluting human fibronectin, such as human fibronectin sold by Becton, Dickinson & Co. of Franklin Lakes, N.J. (BD) (Cat#354008), in Dulbecco's phosphate buffered saline (DPBS) to a protein concentration of 5 µg/mL to about 200 µg/mL. In a particular example, the matrix composition includes a fibronectin fragment, such as RetroNectin®. RetroNectin® is a ~63 kDa protein of (574 amino acids) that contains a central cell-binding domain (type III repeat, 8,9,10), a high affinity heparin-binding domain II (type III repeat, 12,13,14), and CS1 site within the alternatively spliced IIICS region of human fibronectin.

In some other embodiments, the matrix composition preferably includes laminin. For example, a suitable matrix composition may be prepared by diluting laminin (Sigma-Aldrich (St. Louis, Mo.); Cat#L6274 and L2020) in Dulbecco's phosphate buffered saline (DPBS) to a protein concentration of 5 µg/ml to about 200 µg/ml.

In some embodiments, the matrix composition is xeno-free, in that the matrix is or its component proteins are only of human origin. This may be desired for certain research applications. For example in the xeno-free matrix to culture human cells, matrix components of human origin may be used, wherein any non-human animal components may be excluded. In certain aspects, Matrigel™ may be excluded as a substrate for reprogramming into human iPS cells. Matrigel™ is a gelatinous protein mixture secreted by mouse tumor cells and is commercially available from BD Biosciences (New Jersey, USA). This mixture resembles the complex extracellular environment found in many tissues and is used frequently by cell biologists as a substrate for cell culture, but it may introduce undesired xeno antigens or contaminants.

D. Signaling Inhibitors for Reprogramming

In certain aspects of the invention, during at least part of the reprogramming process, the cell may be maintained in the presence or absence of one or more signaling inhibitors which inhibit a signal transducer involved in a signaling cascade, e.g., in the presence of a MEK inhibitor, a GSK3 inhibitor, a TGF-β receptor inhibitor, and/or a myosin II ATPase inhibitor, or inhibitor of other signal transducers within these same pathways. In certain aspects, ROCK inhibitors, such as HA-100 or H1152, may be used to facilitate clonal expansion of reprogrammed cells and resulting iPS cells. High concentration of FGF, in combination with specific reprogramming medium such as conditioned human ES cell culture medium or serum-free N2B27 medium, may also be used to increase reprogramming efficiency. In preferably aspects, the medium is defined or xeno-free.

In certain embodiments, in addition to introducing the cells with reprogramming factors (e.g. two, three or more, as described herein) by exogenous episomal genetic elements, the cells are treated with a reprogramming medium comprising: a MEK inhibitor, a TGF-β receptor inhibitor, a GSK3 inhibitor, a myosin II ATPase inhibitor, and/or LIF, with the advantages such as improving reprogramming efficiency and kinetics and facilitating iPS cell identification in the primary reprogramming culture, thus preserving iPS cell clonality.

It will be understood that in these aspects and embodiments, other signaling inhibitors which inhibit a signaling component of the same signaling pathway (e.g. ERK1 or ERK2 cascade) may be substituted where desired for the MEK inhibitor. This may include inhibition of an upstream stimulus of the MAPK pathway, in particular through the FGF receptor (Ying, 2008). Likewise, the GSK3 inhibitor may be substituted where desired for other inhibitors of GSK3-related signaling pathways, such as insulin synthesis and Wnt/β-catenin signaling; the LIF may be substituted where desired for other activators of Stat3 or gp130 signaling.

Such a signaling inhibitor, e.g., a MEK inhibitor, a GSK3 inhibitor, a TGF-β receptor inhibitor, may be used at an effective concentration of at least or about 0.02, 0.05, 0.1, 0.2, 0.5, 1, 2, 3, 4, 5, 10, 15, 20, 25, 30, 35, 40, 45, 50, 100, 150, 200, 500 to about 1000 µM, or any range derivable therein.

Inhibitors may be provided or obtained by those skilled in the art by conventional means or from conventional sources (see also WO2007113505).

1. Glycogen Synthase Kinase 3 Inhibitor

Glycogen synthase kinase 3 (GSK-3) is a serine/threonine protein kinase that mediates the addition of phosphate molecules on certain serine and threonine amino acids in particular cellular substrates. The phosphorylation of these other proteins by GSK-3 usually inhibits the target protein (also called the "substrate"). As mentioned, GSK-3 is known for phosphorylating and thus inactivating glycogen synthase. It has also been implicated in the control of cellular response to damaged DNA and Wnt signaling. GSK-3 also phosphorylates Ci in the Hedgehog (Hh) pathway, targeting it for proteolysis to an inactive form. In addition to glycogen synthase, GSK-3 has many other substrates. However, GSK-3 is unusual among the kinases in that it usually requires a "priming kinase" to first phosphorylate a substrate.

The consequence of GSK-3 phosphorylation is usually inhibition of the substrate. For example, when GSK-3 phosphorylates another of its substrates, the NFAT family of transcription factors, these transcription factors cannot translocate to the nucleus and are therefore inhibited. In addition to its important role in the Wnt signaling pathway, which is required for establishing tissue patterning during development, GSK-3 is also critical for the protein synthesis that is induced in settings such as skeletal muscle hypertrophy. Its roles as an NFAT kinase also places it as a key regulator of both differentiation and cellular proliferation.

GSK3 inhibition may refer to inhibition of one or more GSK3 enzymes. The family of GSK3 enzymes is well-known and a number of variants have been described (see e.g. Schaffer et al., 2003). In specific embodiments GSK3-β is inhibited. GSK3-α inhibitors are also suitable, and in certain aspects inhibitors for use in the invention inhibit both GSK3-α and GSK3-β.

Inhibitors of GSK3 can include antibodies that bind, dominant negative variants of, and siRNA and antisense nucleic acids that target GSK3. Examples of GSK3 inhibitors are described in Bennett et al. (2002) and in Ring et al. (2003).

Specific examples of GSK3 inhibitors include, but are not limited to, Kenpaullone, 1-Azakenpaullone, CHIR99021, CHIR98014, AR-A014418 (see, e.g., Gould et al., 2004), CT 99021 (see, e.g., Wagman, 2004), CT 20026 (see, Wagman, supra), SB415286, SB216763 (see, e.g., Martin et al., 2005), AR-A014418 (see, e.g., Noble et al., 2005), lithium (see, e.g., Gould et al., 2003), SB 415286 (see, e.g., Frame et al., 2001) and TDZD-8 (see, e.g., Chin et al., 2005). Further exemplary GSK3 inhibitors available from Calbiochem (see, e.g., Dalton et al., WO2008/094597, herein incorporated by reference), include but are not limited to BIO (2'Z,3'£)-6-Bromomdirubm-3'-oxime (GSK3 Inhibitor IX); BIO-Acetoxime (2'Z,3'E)-6-Bromoindirubin-3'-acetoxime (GSK3 Inhibitor X); (5-Methyl-1H-pyrazol-3-yl)-(2-phenylquinazolin-4-yl)amine (GSK3-Inhibitor XIII); Pyridocarbazole-cyclopenadienylruthenium complex (GSK3 Inhibitor XV); TDZD-8 4-Benzyl-2-methyl-1,2,4-thiadiazolidine-3,5-dione (GSK3beta Inhibitor I); 2-Thio(3-iodobenzyl)-5-(1-pyridyl)-[1,3,4]-oxadiazole (GSK3beta Inhibitor II); OTDZT 2,4-Dibenzyl-5-oxothiadiazolidine-3-thione (GSK3beta Inhibitor III); alpha-4-Dibromoacetophenone (GSK3beta Inhibitor VII); AR-AO 14418 N-(4-Methoxybenzyl)-N'-(5-nitro-1,3-thiazol-2-yl)urea (GSK-3beta Inhibitor VIII); 3-(1-(3-Hydroxypropyl)-1H-pyrrolo[2,3-b]pyridin-3-yl]-4-pyrazin-2-yl-pyrrole-2,5-dione (GSK-3beta Inhibitor XI); TWS1 19 pyrrolopyrimidine compound (GSK3beta Inhibitor XII); L803 H-KEAPP APPQSpP-NH2 or its Myristoylated form (GSK3beta Inhibitor XIII); 2-Chloro-1-(4,5-dibromo-thiophen-2-yl)-ethanone (GSK3beta Inhibitor VI); AR-AO144-18; SB216763; and SB415286.

GSK3 inhibitors can activate, for example, the Wnt/β-catenin pathway. Many of β-catenin downstream genes co-regulate pluripotency gene networks. For example, a GSK inhibitor activates cMyc expression as well as enhances its protein stability and transcriptional activity. Thus, in some embodiments, GSK3 inhibitors can be used to stimulate endogenous Myc polypeptide expression in a cell, thereby eliminating the need for Myc expression to induce pluripotency.

In addition, the structure of the active site of GSK3-β has been characterized and key residues that interact with specific and non-specific inhibitors have been identified (Bertrand et al., 2003). This structural characterization allows additional GSK inhibitors to be readily identified.

The inhibitors used herein are preferably specific for the kinase to be targeted. The inhibitors of certain embodiments are specific for GSK3-β and GSK3-α, substantially do not inhibit erk2 and substantially do not inhibit cdc2. Preferably the inhibitors have at least 100 fold, more preferably at least 200 fold, very preferably at least 400 fold selectivity for human GSK3 over mouse erk2 and/or human cdc2, measured as ratio of $IC_{50}$ values; here, reference to GSK3 $IC_{50}$ values refers to the mean values for human GSK3-β and GSK3-α. Good results have been obtained with CHIR99021 which is specific for GSK3. Suitable concentrations for use of CHIR99021 are in the range 0.01 to 100, preferably 0.1 to 20, more preferably 0.3 to 10 micromolar.

2. MEK Inhibitor

MEK inhibitors, which include inhibitors of mitogen-activated protein kinase kinase (MAPK/ERK kinase or MEK) or its related signaling pathways like MAPK cascade, may be used in certain aspects of the invention. Mitogen-activated protein kinase kinase (sic) is a kinase enzyme which phosphorylates mitogen-activated protein kinase. It is also known as MAP2K. Extracellular stimuli lead to activation of a MAP kinase via a signaling cascade ("MAPK cascade") composed of MAP kinase, MAP kinase kinase (MEK, MKK, MEKK, or MAP2K), and MAP kinase kinase kinase (MKKK or MAP3K).

A MEK inhibitor herein refers to MEK inhibitors in general. Thus, a MEK inhibitor refers to any inhibitor of a member of the MEK family of protein kinases, including MEK1, MEK2 and MEK5. Reference is also made to MEK1, MEK2 and MEK5 inhibitors. Examples of suitable MEK inhibitors, already known in the art, include the MEK1 inhibitors PD184352 and PD98059, inhibitors of MEK1 and MEK2 U0126 and SL327, and those discussed in Davies et al. (2000).

In particular, PD184352 and PD0325901 have been found to have a high degree of specificity and potency when compared to other known MEK inhibitors (Bain et al., 2007). Other MEK inhibitors and classes of MEK inhibitors are described in Zhang et al. (2000).

Inhibitors of MEK can include antibodies to, dominant negative variants of, and siRNA and antisense nucleic acids that suppress expression of MEK. Specific examples of MEK inhibitors include, but are not limited to, PD0325901 (see, e.g., Rinehart et al., 2004), PD98059 (available, e.g., from Cell Signaling Technology), U0126 (available, for example, from Cell Signaling Technology), SL327 (available, e.g., from Sigma-Aldrich), ARRY-162 (available, e.g., from Array Biopharma), PD184161 (see, e.g., Klein et al., 2006), PD184352 (CI-1040) (see, e.g., Mattingly et al., 2006), sunitinib (see, e.g., Voss, et al., US2008004287 incorporated herein by reference), sorafenib (see, Voss supra), Vandetanib (see, Voss supra), pazopanib (see, e.g., Voss supra), Axitinib (see, Voss supra) and PTK787 (see, Voss supra).

Currently, several MEK inhibitors are undergoing clinical trial evaluations. CI-1040 has been evaluate in Phase I and II clinical trials for cancer (see, e.g., Rinehart et al., 2004). Other MEK inhibitors being evaluated in clinical trials include PD 184352 (see, e.g., English et al., 2002), BAY 43-9006 (see, e.g., Chow et al., 2001), PD-325901 (also PD0325901), GSK1 120212, ARRY-438162, RDEA1 19, AZD6244 (also ARRY-142886 or ARRY-886), RO5126766, XL518 and AZD8330 (also ARRY-704).

Inhibition of MEKs can also be conveniently achieved using RNA-mediated interference (RNAi). Typically, a double-stranded RNA molecule complementary to all or part of a MEK gene is introduced into pluripotent cells, thus promoting specific degradation of MEK-encoding mRNA molecules. This post-transcriptional mechanism results in reduced or abolished expression of the targeted MEK gene. Suitable techniques and protocols for achieving MEK inhibition using RNAi are known.

A number of assays for identifying kinase inhibitors, including GSK3 inhibitors and MEK inhibitors, are known. For example, Davies et al. (2000) describes kinase assays in which a kinase is incubated in the presence of a peptide substrate and radiolabeled ATP. Phosphorylation of the substrate by the kinase results in incorporation of the label into the substrate. Aliquots of each reaction are immobilized on phosphocellulose paper and washed in phosphoric acid to remove free ATP. The activity of the substrate following incubation is then measured and provides an indication of kinase activity. The relative kinase activity in the presence and absence of candidate kinase inhibitors can be readily determined using such an assay. Downey et al. (1996) also describes assays for kinase activity which can be used to identify kinase inhibitors.

3. TGF-β Receptor Inhibitor

TGF-β receptor inhibitors may include any inhibitors of TGF signaling in general or inhibitors specific for TGF-β receptor (e.g., ALK5) inhibitors, which can include antibodies to, dominant negative variants of, and siRNA and antisense nucleic acids that suppress expression of, TGF beta receptors (e.g., ALK5). Exemplary TGFβ receptor/ALK5 inhibitors include, but are not limited to, SB431542 (see, e.g., Inman et al., 2002), A-83-01, also known as 3-(6-Methyl-2-pyridinyl)-N-phenyl-4-(4-quinolinyl)-1H-pyrazole-1-carbothioamide (see, e.g., Tojo et al., 2005, and commercially available from, e.g., Toicris Bioscience); 2-(3-(6-Methylpyridin-2-yl)-1H-pyrazol-4-yl)-1,5-naphthyridine, Wnt3a/BIO (see, e.g., Dalton, et al., WO2008/094597, herein incorporated by reference), BMP4 (see, Dalton, supra), GW788388 (−(4-[3-(pyridin-2-yl)-1H-pyrazol-4-yl] pyridin-2-yl}-N-(tetrahydro-2H-pyran-4-yl)benzamide) (see, e.g., Gellibert et al., 2006), SM16 (see, e.g., Suzuki et al., 2007), IN-1130 (3-((5-(6-methylpyridin-2-yl)-4-(quinoxalin-6-yl)-1H-imidazol-2-yl)methyl)benzamide) (see, e.g., Kim et al., 2008), GW6604 (2-phenyl-4-(3-pyridin-2-yl-1H-pyrazol-4-yl)pyridine) (see, e.g., de Gouville et al., 2006), SB-505124 (2-(5-benzo[1,3]dioxol-5-yl-2-tert-butyl-3H-imidazol-4-yl)-6-methylpyridine hydrochloride) (see, e.g., DaCosta et al., 2004) and pyrimidine derivatives (see, e.g., those listed in Stiefl et al., WO2008/006583, herein incorporated by reference).

Further, while an "ALK5 inhibitor" is not intended to encompass non-specific kinase inhibitors, an "ALK5 inhibitor" should be understood to encompass inhibitors that inhibit ALK4 and/or ALK7 in addition to ALK5, such as, for example, SB-431542 (see, e.g., Inman et al., 2002). Without intending to limit the scope of the invention, it is believed that ALK5 inhibitors affect the mesenchymal to epithelial conversion/transition (MET) process. TGFβ/activin pathway is a driver for epithelial to mesenchymal transition (EMT). The inventor contemplates that inhibiting the TGFβ/activin pathway can facilitate MET (i.e., reprogramming) process.

It is believed that inhibition of the TGFβ/activin pathway will have similar effects. Thus, any inhibitor (e.g., upstream or downstream) of the TGFβ/activin pathway can be used in combination with, or instead of, TGF-β/ALK5 inhibitors as described herein. Exemplary TGFβ/activin pathway inhibitors include but are not limited to: TGFβ receptor inhibitors, inhibitors of SMAD 2/3 phosphorylation, inhibitors of the interaction of SMAD 2/3 and SMAD 4, and activators/agonists of SMAD 6 and SMAD 7. Furthermore, the categorizations described herein are merely for organizational purposes and one of skill in the art would know that compounds can affect one or more points within a pathway, and thus compounds may function in more than one of the defined categories.

TGF beta receptor inhibitors can include antibodies to, dominant negative variants of, and siRNA or antisense nucleic acids that target TGF beta receptors. Specific examples of inhibitors include but are not limited to SU5416; 2-(5-benzo[1,3]dioxol-5-yl-2-tert-butyl-3H-imidazol-4-yl)-6-methylpyridine hydrochloride (SB-505124); lerdelimumb (CAT-152); metelimumab (CAT-192); GC-1008; ID1 1; AP-12009; AP-11014; LY550410; LY580276; LY364947; LY2109761; SB-505124; SB-431542; SD-208; SM16; NPC-30345; Ki26894; SB-203580; SD-093; Gleevec; 3,5,7,2',4'-pentahydroxyflavone (Morin); activin-M108A; P144; soluble TBR2-Fc; and antisense transfected tumor cells that target TGF beta receptors (See, e.g., Wrzesinski et al., 2007; Kaminska et al., 2005; and Chang et al., 2007.)

4. ROCK Inhibitors

Pluripotent stem cells, especially human ES cells and iPS cells, are vulnerable to apoptosis upon cellular detachment and dissociation, which are important for clonal isolation or expansion and differentiation induction. Recently, a small class of molecules have been found to increase clonal efficiency and survival of dissociated pluripotent stem cells, such as Rho-associated kinase (ROCK) inhibitors, which are inhibitors for ROCK-related signaling pathways, for example, Rho-specific inhibitors, ROCK-specific inhibitors or myosin II-specific inhibitors. In certain aspects of the invention, ROCK inhibitors may be used for culturing and passaging of pluripotent stem cells and/or differentiation of the stem cells. Therefore, ROCK inhibitors could be present in any cell culture medium in which pluripotent stem cells grow, dissociate, form aggregates, or undergo differentiation, such as an adherent culture or suspension culture.

ROCK signaling pathways may include Rho family GTPases; ROCK, a major effector kinase downstream of Rho; Myosin II, the predominant effector downstream of ROCK (Harb et al., 2008); and any intermediate, upstream, or downstream signal processors. ROCK may phosphorylate and inactivate myosin phosphatase target subunit 1 (MYPT1), one of the major downstream targets of ROCK that negatively regulates myosin function through dephosphorylation of myosin regulatory light chain (MRLC).

ROCKs are serine/threonine kinases that serve as a target proteins for Rho (of which three isoforms exist—RhoA, RhoB and RhoC). Theses kinases were initially characterized as mediators of the formation of RhoA-induced stress fibers and focal adhesions. The two ROCK isoforms—ROCK1 (p160ROCK, also called ROKβ) and ROCK2 (ROKα)—are comprised of a N-terminal kinase domain, followed by a coiled-coil domain containing a Rho-binding domain and a pleckstrin-homology domain (PH). Both ROCKs are cytoskeletal regulators, mediating RhoA effects on stress fiber formation, smooth muscle contraction, cell adhesion, membrane ruffling and cell motility. ROCKs may exert their biological activity by targeting downstream molecules, such as myosin II, myosin light chain (MLC), MLC phosphatase (MLCP) and the phosphatase and tensin homolog (PTEN).

Non-limiting examples of ROCK inhibitors include HA-100, Y-27632, H-1152, Fasudil (also referred to as HA1077), Y-30141 (described in U.S. Pat. No. 5,478,838), Wf-536, HA-1077, hydroxyl-HA-1077, GSK269962A, SB-772077-B, and derivatives thereof, and antisense nucleic acid for ROCK, RNA interference inducing nucleic acid (for example, siRNA), competitive peptides, antagonist peptides, inhibitory antibodies, antibody-ScFV fragments, dominant negative variants and expression vectors thereof. Further, since other low molecular compounds are known as ROCK inhibitors, such compounds or derivatives thereof can be also used in embodiments (for example, refer to U.S. Patent Publication Nos. 20050209261, 20050192304, 20040014755, 20040002508, 20040002507, 20030125344 and 20030087919, and International Patent Publication Nos. 2003/062227, 2003/059913, 2003/062225, 2002/076976 and 2004/039796, which are hereby incorporated by reference). In certain aspects of the present invention, a combination of one or two or more of the ROCK inhibitors can also be used.

Rho-specific inhibitors, such as *Clostridium botulinum* C3 exoenzyme, and/or Myosin II-specific inhibitors may also be used as a ROCK inhibitor in certain aspects of the invention.

E. Hypoxic Conditions

Low oxygen could be used during the entire expansion stage prior to reprogramming to favor maintenance of the progenitor-like state and possibly at least part of the reprogramming stage. First, as cells expand they tend to drift away from being more progenitor-like to becoming more differentiated (i.e., the level of CD34 expression decreases over time). The low oxygen condition mimics the microenvironment typical of hematopoietic progenitor cells (HPs) and appears to slow the differentiation of the progenitor cells (Eliasson and Jonsson, 2010). Low oxygen used herein may be at a level of about 2% or may be within a range of about 1-7%. In a further aspect, low $O_2$ may also be used during the reprogramming stage to encourage iPS formation (Yoshida et al., 2009).

V. Episomal Genetic Elements

In certain aspects of the present invention, reprogramming factors are expressed from expression cassettes comprised in one or more exogenous episomal genetic elements (see U.S. Patent Publication 2010/0003757 and U.S. Application No. 61/258,120, incorporated herein by reference).

Induction of pluripotent stem cells from human somatic cells has been achieved using retroviruses or lentiviral vectors for ectopic expression of reprogramming genes. Recombinant retroviruses such as the Moloney murine leukemia virus have the ability to integrate into the host genome in a stable fashion. They contain a reverse transcriptase which allows integration into the host genome. Lentiviruses are a subclass of retroviruses. They are widely adapted as vectors thanks to their ability to integrate into the genome of non-dividing as well as dividing cells. The viral genome in the form of RNA is reverse-transcribed when the virus enters the cell to produce DNA, which is then inserted into the genome at a random position by the viral integrase enzyme. Therefore, current technology of successful reprogramming is dependent on integration-based viral approaches.

However, with the present technology, targeted integration is still no routine (Bode et al., 2000) and the conventional alternative, random integration, may lead to insertional mutagenesis with unpredictable consequences in induced pluripotent stem cells. For the same reasons expression of the transgene cannot be controlled since it is dependent on the chromatin context of the integration site (Baer et al., 2000). High level of expression can only be achieved at favorable genomic loci but the danger exists that integration into highly expressed sites interferes with vital cellular functions of induced pluripotent stem cells.

In addition, there is increasing evidence for the existence of cellular defense mechanisms against foreign DNA which operate by down-regulating transgenes in a process that is accompanied by DNA methylation (Bingham, 1997, Garrick et al., 1998). Furthermore, viral components may act along with other factors to transform cells. Accompanied by the continual expression from a number of viral genes, the persistence of at least part of the viral genome within the cell may cause cell transformation. These genes may interfere with a cell's signaling pathway causing the observed phenotypic changes of the cell, leading to a transformed cell showing increased cell division, which is favorable to the virus.

Therefore, in certain embodiments, the present invention develops novel methods to generate induced pluripotent stem cells essentially free of exogenous genetic elements, such as from retroviral or lentiviral vector elements used in the previous methods. These methods in the present invention make use of extra-chromosomally replicating vectors, or vectors capable of replicating episomally (see U.S. application Ser. No. 12/478,154, incorporated herein by reference), in combination with culturing reprogrammed cells in the presence of cellular signaling inhibitors to achieve optimal reprogramming efficiency and kinetics.

A number of DNA viruses, such as adenoviruses, Simian vacuolating virus 40 (SV40), bovine papilloma virus (BPV), or budding yeast ARS (Autonomously Replicating Sequences)-containing plasmids replicate extra-chromosomally in mammalian cells. These episomal plasmids are intrinsically free from all these disadvantages (Bode et al., 2001) associated with integrating vectors. A lymphotrophic herpes virus-based system including Epstein Barr Virus (EBV) may also replicate extra-chromosomally and help deliver reprogramming genes to somatic cells.

For example, the episomal vector-based approach used in the invention extracts robust elements necessary for the successful replication and maintenance of an EBV element-based system without compromising the system's tractability in a clinical setting as described in detail below. The useful EBV elements are OriP and EBNA-1, or their variants or functional equivalents. An additional advantage of this system is that these exogenous elements will be lost with time after being introduced into cells, leading to self-sustained iPS cells essentially free of these elements.

A. Episomal Vectors

These reprogramming methods may make use of extra-chromosomally replicating vectors (i.e., episomal vectors), which are vectors capable of replicating episomally to make iPS cells essentially free of exogenous vector or viral elements (see U.S. Application No. 61/058,858, incorporated herein by reference; Yu et al., 2009). A number of DNA viruses, such as adenoviruses, Simian vacuolating virus 40 (SV40) or bovine papilloma virus (BPV), or budding yeast ARS (Autonomously Replicating Sequences)-containing plasmids replicate extra-chromosomally or episomally in mammalian cells. These episomal plasmids are intrinsically free from all these disadvantages (Bode et al., 2001) associated with integrating vectors. For example, a lymphotrophic herpes virus-based including or Epstein Barr Virus (EBV) as defined above may replicate extra-chromosomally and help deliver reprogramming genes to somatic cells.

For example, the plasmid-based approach used in the invention may extract robust elements necessary for the successful replication and maintenance of an EBV element-based system without compromising the system's tractability in a clinical setting as described in detail below. The essential EBV elements are OriP and EBNA-1 or their variants or functional equivalents. An additional advantage of this system is that these exogenous elements will be lost with time after being introduced into cells, leading to self-sustained iPS cells essentially free of exogenous elements.

The use of plasmid- or liposome-based extra-chromosomal vectors, e.g., oriP-based vectors, and/or vectors encoding a derivative of EBNA-1 permit large fragments of DNA to be introduced to a cell and maintained extra-chromosomally, replicated once per cell cycle, partitioned to daughter cells efficiently, and elicit substantially no immune response. In particular, EBNA-1, the only viral protein required for the replication of the oriP-based expression vector, does not elicit a cellular immune response because it has developed an efficient mechanism to bypass the processing required for presentation of its antigens on MHC class I molecules (Levitskaya et al., 1997). Further, EBNA-1 can act in trans to enhance expression of the cloned gene, inducing expression of a cloned gene up to 100-fold in some cell lines (Langle-Rouault et al., 1998; Evans et al., 1997). Finally, the manufacture of such oriP-based expression vectors is inexpensive.

Other extra-chromosomal vectors include other lymphotrophic herpes virus-based vectors. Lymphotrophic herpes virus is a herpes virus that replicates in a lymphoblast (e.g., a human B lymphoblast) and becomes a plasmid for a part of its natural life-cycle. Herpes simplex virus (HSV) is not a "lymphotrophic" herpes virus. Exemplary lymphotrophic herpes viruses include, but are not limited to EBV, Kaposi's sarcoma herpes virus (KSHV); Herpes virus saimiri (HS) and Marek's disease virus (MDV). Also other sources of episome-base vectors are contemplated, such as yeast ARS, adenovirus, SV40, or BPV.

B. Epstein-Barr Virus

The Epstein-Barr Virus (EBV), also called Human herpesvirus 4 (HHV-4), is a virus of the herpes family (which includes Herpes simplex virus and Cytomegalovirus), and is one of the most common viruses in humans. EBV maintains its genome extra-chromosomally and works in collaboration with host cell machinery for efficient replication and maintenance (Lindner and Sugden, 2007), relying solely on two essential features for its replication and its retention within cells during cell division (Yates et al. 1985; Yates et al. 1984). One element, commonly referred to as oriP, exists in cis and serves as the origin of replication. The other factor, EBNA-1, functions in trans by binding to sequences within oriP to promote replication and maintenance of the plasmid DNA. As a non-limiting example, certain aspects of the invention extract these two features and use them in the context of a vector to shuttle the genes necessary for reprogramming somatic cells to facilitate the replication and sustained expression of these genes over conventional plasmids.

C. Replication Origin

In certain aspects, a replication origin of EBV, OriP, may be used. OriP is the site at or near which DNA replication initiates and is composed of two cis-acting sequences approximately 1 kilobase pair apart known as the family of repeats (FR) and the dyad symmetry (DS).

FR is composed of 21 imperfect copies of a 30 bp repeat and contains 20 high affinity EBNA-1-binding sites. When FR is bound by EBNA-1, it both serves as a transcriptional enhancer of promoters in cis up to 10 kb away (Reisman and Sugden, 1986; Yates, 1988; Sugden and Warren, 1989; Wysokenski and Yates, 1989; Gahn and Sugden, 1995; Kennedy and Sugden, 2003; Altmann et al., 2006), and contributes to the nuclear retention and faithful maintenance of FR containing plasmids (Langle-Rouault et al., 1998; Kirchmaier and Sugden, 1995; Wang et al., 2006; Nanbo and Sugden, 2007). The efficient partitioning of oriP plasmids is also likely attributable to FR. While the virus has evolved to maintain 20 EBNA-1-binding sites in FR, efficient plasmid maintenance requires only seven of these sites, and can be reconstituted by a polymer of three copies of DS, having a total of 12 EBNA-1-binding sites (Wysokenski and Yates, 1989).

The dyad symmetry element (DS) is sufficient for initiation of DNA synthesis in the presence of EBNA-1 (Aiyar et al., 1998; Yates et al., 2000), and initiation occurs either at or near DS (Gahn and Schildkraut, 1989; Niller et al., 1995). Termination of viral DNA synthesis is thought to occur at FR, because when FR is bound by EBNA-1 it functions as a replication fork barrier as observed by 2D gel electrophoresis (Gahn and Schildkraut, 1989; Ermakova et al., 1996; Wang et al., 2006). Initiation of DNA synthesis from DS is licensed to once-per-cell-cycle (Adams, 1987; Yates and Guan, 1991), and is regulated by the components of the cellular replication system (Chaudhuri et al., 2001; Ritzi et al., 2003; Dhar et al., 2001; Schepers et al., 2001; Zhou et al., 2005; Julien et al., 2004). DS contains four EBNA-1-binding sites, albeit with lower affinity than those found in FR (Reisman et al., 1985). The topology of DS is such that the four binding sites are arranged as two pairs of sites, with 21 bp center-to-center spacing between each pair and 33 bp center-to-center spacing between the two non-paired internal binding sites (Baer et al., 1984; Rawlins et al., 1985).

The functional roles of the elements within DS have been confirmed by studies of another region of EBV's genome, termed Rep*, which was identified as an element that can substitute for DS inefficiently (Kirchmaier and Sugden, 1998). Polymerizing Rep* eight times yielded an element as efficient as DS in its support of replication (Wang et al., 2006). Biochemical dissection of Rep* identified a pair of EBNA-1-binding sites with a 21 bp center-to-center spacing critical for its replicative function (ibid). The minimal replicator of Rep* was found to be the pair of EBNA-1-binding sites, as replicative function was retained even after all flanking sequences in the polymer were replaced with sequences derived from lambda phage. Comparisons of DS and Rep* have revealed a common mechanism: these replicators support the initiation of DNA synthesis by recruiting the cellular replicative machinery via a pair of appropriately spaced sites, bent and bound by EBNA-1.

There are other extra-chromosomal, licensed plasmids that replicate in mammalian cells that are unrelated to EBV and in some ways appear similar to the zone of initiation within the Raji strain of EBV. Hans Lipps and his colleagues have developed and studied plasmids that contain "nuclear scaffold/matrix attachment regions" (S/MARs) and a robust transcriptional unit (Piechaczek et al., 1999; Jenke et al., 2004). Their S/MAR is derived from the human interferon-beta gene, is A/T rich, and operationally defined by its association with the nuclear matrix and its preferential unwinding at low ionic strength or when embedded in supercoiled DNA (Bode et al., 1992). These plasmids replicate semiconservatively, bind ORC proteins, and support the initiation of DNA synthesis effectively randomly throughout their DNA (Schaarschmidt et al., 2004). They are efficiently maintained in proliferating hamster and human cells without drug selection and when introduced into swine embryos can support expression of GFP in most tissues of fetal animals (Manzini et al., 2006).

D. Trans-Acting Factor

A particular example of the trans-acting factor could be Epstein Barr nuclear antigen 1 (EBNA-1), which is a DNA-binding protein that binds to FR and DS of oriP or Rep* to facilitate replication and faithful partitioning of the EBV-based vector to daughter cells independent of, but in concert with, cell chromosomes during each cell division.

The 641 amino acids (AA) of EBNA-1 have been categorized into domains associated with its varied functions by mutational and deletional analyses. Two regions, between AA40-89 and AA329-378 are capable of linking two DNA elements in cis or in trans when bound by EBNA-1, and have thus been termed Linking Region 1 and 2 (LR1, LR2) (Middleton and Sugden, 1992; Frappier and O'Donnell, 1991; Su et al., 1991; Mackey et al., 1995). Fusing these domains of EBNA-1 to GFP homes the GFP to mitotic chromosomes (Marechal et al., 1999; Kanda et al., 2001). LR1 and LR2 are functionally redundant for replication; a deletion of either one yields a derivative of EBNA-1 capable of supporting DNA replication (Mackey and Sugden, 1999; Sears et al., 2004). LR1 and LR2 are rich in arginine and glycine residues, and resemble the AT-hook motifs that bind A/T rich DNA (Aravind and Landsman, 1998), (Sears et al., 2004). An in vitro analysis of LR1 and LR2 of EBNA-1 has demonstrated their ability to bind to A/T rich DNA (Sears et al., 2004). When LR1, containing one such AT-hook, was fused to the DNA-binding and dimerization domain of EBNA-1, it was found to be sufficient for DNA replication of oriP plasmids, albeit less efficiently than the wild-type EBNA-1 (ibid).

LR1 and LR2 do differ, though. The C-terminal half of LR1 is composed of amino acids other than the repeated Arg-Gly of the N-terminal half, and is termed unique region 1 (URI). URI is necessary for EBNA-1 to activate transcription efficiently from transfected and integrated reporter DNAs containing FR (Wu et al., 2002; Kennedy and Sugden, 2003; Altmann et al., 2006). URI is also essential for the efficient transformation of B-cells infected by EBV. When a derivative of EBNA-1 lacking this domain replaces the wild-type protein in the context of the whole virus, these derivative viruses have 0.1% of the transforming ability of the wild-type virus (Altmann et al., 2006).

LR2 is not required for EBNA-1's support of oriP replication (Shire et al., 1999; Mackey and Sugden, 1999; Sears et al., 2004). Additionally, the N-terminal half of EBNA-1 can be replaced with cellular proteins containing AT-hook motifs, such as HMGA1a, and still retain replicative function (Hung et al., 2001; Sears et al., 2003; Altmann et al., 2006). These findings indicate that it likely is the AT-hook activities of LR1 and LR2 that are required for the maintenance of oriP in human cells.

A third of EBNA-1's residues (AA91-328) consist of glycine-glycine-alanine (GGA) repeats, implicated in EBNA-1's ability to evade the host immune response by inhibiting proteosomal degradation and presentation (Levitskaya et al., 1995; Levitskaya et al., 1997). These repeats have also been found to inhibit translation of EBNA-1 in vitro and in vivo (Yin et al., 2003). However, the deletion of much of this domain has no apparent effect on functions of EBNA-1 in cell culture, making the role that this domain plays difficult to elucidate.

A nuclear localization signal (NLS) is encoded by AA379-386, which also associates with the cellular nuclear importation machinery (Kim et al., 1997; Fischer et al., 1997). Sequences within the Arg-Gly rich regions of LR1 and LR2 may also function as NLSs due to their highly basic content.

Lastly, the C-terminus (AA458-607) encodes the overlapping DNA-binding and dimerization domains of EBNA-1. The structure of these domains bound to DNA has been solved by X-ray crystallography, and was found to be similar to the DNA-binding domain of the E2 protein of papillomaviruses (Hegde et al., 1992; Kim et al., 2000; Bochkarev et al., 1996).

In specific embodiments of the invention, a reprogramming vector will contain both oriP and an abbreviated sequence encoding a version of EBNA-1 competent to support plasmid replication and its proper maintenance during cell division. The highly repetitive sequence within the amino-terminal one-third of wild-type EBNA-1 and removal of a 25 amino-acid region that has demonstrated toxicity in various cells are dispensable for EBNA-1's trans-acting function associated with oriP (Yates et al. 1985; Kennedy et al. 2003). Therefore, the abbreviated form of EBNA-1, known as deltaUR1, could be used alongside oriP within this episomal vector-based system in one embodiment.

In certain aspects, a derivative of EBNA-1 that may be used in the invention is a polypeptide which, relative to a corresponding wild-type polypeptide, has a modified amino acid sequence. The modifications include the deletion, insertion or substitution of at least one amino acid residue in a region corresponding to the unique region (residues about 65 to about 89) of LR1 (residues about 40 to about 89) in EBNA-1, and may include a deletion, insertion and/or substitution of one or more amino acid residues in regions corresponding to other residues of EBNA-1, e.g., about residue 1 to about residue 40, residues about 90 to about 328 ("Gly-Gly-Ala" repeat region), residues about 329 to about 377 (LR2), residues about 379 to about 386 (NLS), residues about 451 to about 608 (DNA binding and dimerization), or residues about 609 to about 641, so long as the resulting derivative has the desired properties, e.g., dimerizes and binds DNA containing an on corresponding to oriP, localizes to the nucleus, is not cytotoxic, and activates transcription from an extra-chromosomal but does not substantially active transcription from an integrated template.

E. Residue-Free Feature

Importantly, the replication and maintenance of oriP-based episomal vector is imperfect and is lost precipitously (25% per cell division) from cells within the first two weeks of its being introduced into cells; however, those cells that retain the plasmid lose it less frequently (3% per cell division) (Leight and Sugden, 2001; Nanbo and Sugden, 2007). Once selection for cells harboring the plasmid is removed, plasmids will be lost during each cell division until all of them have been eliminated over time without leaving a footprint of its former existence within the resulting daughter cells. Certain aspects of the invention make use of this footprint-less feature of the oriP-based system as an alternative to the current viral-associated approach to deliver genes to generate iPS cells. Other extra-chromosomal vectors will also be lost during replication and propagation in host cells and could also be employed in the present invention. In certain aspects, method for removal of exogenous episomal vector elements or selection of iPS cells essentially free of exogenous genetic elements may be used.

VI. Vector Construction and Delivery

In certain embodiments, reprogramming vectors could be constructed to comprise additional elements in addition to nucleic acid sequences encoding reprogramming factors as described above in cells. Details of components of these vectors and delivery methods are disclosed below.

A. Vector

One of skill in the art would be well equipped to construct a vector through standard recombinant techniques (see, for example, Maniatis et al., 1988 and Ausubel et al., 1994, both incorporated herein by reference).

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide.

Such components also might include markers, such as detectable and/or selection markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

B. Regulatory Elements

Eukaryotic expression cassettes included in the vectors particularly contain (in a 5'-to-3' direction) a eukaryotic transcriptional promoter operably linked to a protein-coding sequence, splice signals including intervening sequences, and a transcriptional termination/polyadenylation sequence.

i. Promoter/Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

Promoters suitable for use in EBNA 1-encoding vector of the invention are those that direct the expression of the expression cassettes encoding the EBNA 1 protein to result in sufficient steady-state levels of EBNA 1 protein to stably maintain EBV oriP-containing vectors. Promoters are also used for efficient expression of expression cassettes encoding reprogramming factors.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, through world wide web at epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Non-limiting examples of promoters include early or late viral promoters, such as, SV40 early or late promoters, cytomegalovirus (CMV) immediate early promoters, Rous Sarcoma Virus (RSV) early promoters; eukaryotic cell promoters, such as, e.g., beta actin promoter (Ng, 1989;

Quitsche et al., 1989), GADPH promoter (Alexander et al., 1988, Ercolani et al., 1988), metallothionein promoter (Karin et al., 1989; Richards et al., 1984); and concatenated response element promoters, such as cyclic AMP response element promoters (cre), serum response element promoter (sre), phorbol ester promoter (TPA) and response element promoters (tre) near a minimal TATA box. It is also possible to use human growth hormone promoter sequences (e.g., the human growth hormone minimal promoter described at Genbank, accession no. X05244, nucleotide 283-341) or a mouse mammary tumor promoter (available from the ATCC, Cat. No. ATCC 45007). A specific example could be a phosphoglycerate kinase (PGK) promoter.

ii. Protease Cleavage Sites/Self-Cleaving Peptides and Internal Ribosome Binding Sites In certain aspects, according to the present invention, the genes encoding markers or reprogramming proteins may be connected to one another by a sequence (there may be more than one) coding for a protease cleavage site (i.e. a sequence comprising the recognition site of a protease) or at least one self-cleaving peptide. For example, a polycistronic message comprising at least two reprogramming factor genes may be used in certain aspects of the invention (see U.S. Ser. No. 12/539,366, herein incorporated by reference).

According to a certain embodiment of the present invention the protease(s) capable of cleaving the cleavage sites encoded by the sequence(s) connecting the genes constituting the polycistronic message is/are encoded by the polynucleotide of the present invention. More particularly, the gene(s) encoding the protease(s) is/are part of at least one of the polycistronic message.

Suitable protease cleavages sites and self-cleaving peptides are known to the skilled person (see, e.g., in Ryan et al., 1997; Scymczak et al., 2004). Preferred examples of protease cleavage sites are the cleavage sites of potyvirus NIa proteases (e.g. tobacco etch virus protease), potyvirus HC proteases, potyvirus P1 (P35) proteases, byovirus N1a proteases, byovirus RNA-2-encoded proteases, aphthovirus L proteases, enterovirus 2A proteases, rhinovirus 2A proteases, picorna 3C proteases, comovirus 24K proteases, nepovirus 24K proteases, RTSV (rice tungro spherical virus) 3C-like protease, PY\IF (parsnip yellow fleck virus) 3C-like protease, thrombin, factor Xa and enterokinase. Due to its high cleavage stringency, TEV (tobacco etch virus) protease cleavage sites may be used.

Exemplary self-cleaving peptides (also called "cis-acting hydrolytic elements", CHYSEL; see deFelipe (2002) are derived from potyvirus and cardiovirus 2A peptides. Particular self-cleaving peptides may be selected from 2A peptides derived from FMDV (foot-and-mouth disease virus), equine rhinitis A virus, Thoseá asigna virus and porcine teschovirus.

A specific initiation signal also may be used for efficient translation of coding sequences in a polycistronic message. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

iii. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

iv. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

v. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message.

The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

vi. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

vii. Origins of Replication

In order to propagate a vector in a host cell, it may contain one or more origins of replication sites (often termed "ori"), for example, a nucleic acid sequence corresponding to oriP of EBV as described above or a genetically engineered oriP with a similar or elevated function in differentiation programming, which is a specific nucleic acid sequence at which replication is initiated. Alternatively a replication origin of other extra-chromosomally replicating virus as described above or an autonomously replicating sequence (ARS) can be employed.

viii. Selection and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selection marker is one that confers a property that allows for selection. A positive selection marker is one in which the presence of the marker allows for its selection, while a negative selection marker is one in which its presence prevents its selection. An example of a positive selection marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selection markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes as negative selection markers such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selection and screenable markers are well known to one of skill in the art. One feature of the present invention includes using selection and screenable markers to select vector-free cells after the differentiation programming factors have effected a desired altered differentiation status in those cells.

C. Vector Delivery

Introduction of a reprogramming vector into somatic cells with the current invention may use any suitable methods for nucleic acid delivery for transformation of a cell, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

i. Liposome-Mediated Transfection

In a certain embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen). The amount of liposomes used may vary upon the nature of the liposome as well as the cell used, for example, about 5 to about 20 µg vector DNA per 1 to 10 million of cells may be contemplated.

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

ii. Electroporation

In certain embodiments of the present invention, a nucleic acid is introduced into a cell via electroporation. Electroporation involves the exposure of a suspension of cells and DNA to a high-voltage electric discharge. Recipient cells can be made more susceptible to transformation by mechanical wounding. Also the amount of vectors used may vary upon the nature of the cells used, for example, about 5 to about 20 µg vector DNA per 1 to 10 million of cells may be contemplated.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

iii. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

iv. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

VII. Reprogramming Factors

The generation of iPS cells is crucial on the reprogramming factors used for the induction. The following factors or combination thereof could be used in the methods disclosed in the present invention. In certain aspects, nucleic acids encoding Sox and Oct (particularly Oct3/4) will be included into the reprogramming vector. For example, one or more reprogramming vectors may comprise expression cassettes encoding Sox2, Oct4, Nanog and optionally Lin28, or expression cassettes encoding Sox2, Oct4, Klf4 and optionally C-myc or L-myc, or expression cassettes encoding Sox2, Oct4, and optionally Esrrb, or expression cassettes encoding Sox2, Oct4, Nanog, Lin28, Klf4, either C-myc or L-myc, and optionally SV40 Large T antigen. Nucleic acids encoding these reprogramming factors may be comprised in the same expression cassette, different expression cassettes, the same reprogramming vector, or different reprogramming vectors.

Oct4 and certain members of the Sox gene family (Sox1, Sox2, Sox3, and Sox15) have been identified as crucial transcriptional regulators involved in the induction process whose absence makes induction impossible. Additional genes, however, including certain members of the Klf family (Klf1, Klf2, Klf4, and Klf5), the Myc family (C-myc, L-myc, and N-myc), Nanog, and Lin28, have been identified to increase the induction efficiency.

Oct4 (Pou5f1) is one of the family of octamer ("Oct") transcription factors, and plays a crucial role in maintaining pluripotency. The absence of Oct4 in Oct4$^+$ cells, such as blastomeres and embryonic stem cells, leads to spontaneous trophoblast differentiation, and presence of Oct4 thus gives rise to the pluripotency and differentiation potential of embryonic stem cells. Various other genes in the "Oct" family, including Oct4's close relatives, Oct1 and Oct6, fail to elicit induction, thus demonstrating the exclusiveness of Oct-4 to the induction process.

The Sox family of genes is associated with maintaining pluripotency similar to Oct4, although it is associated with multipotent and unipotent stem cells in contrast with Oct4, which is exclusively expressed in pluripotent stem cells. While Sox2 was the initial gene used for reprogramming induction, other genes in the Sox family have been found to work as well in the induction process. Sox1 yields iPS cells with a similar efficiency as Sox2, and genes Sox3, Sox15, and Sox18 also generate iPS cells, although with decreased efficiency.

In embryonic stem cells, Nanog, along with Oct4 and Sox2, is necessary in promoting pluripotency. Therefore, it was surprising when Yamanaka et al. reported that Nanog was unnecessary for induction although Thomson et al. has reported it is possible to generate iPS cells with Nanog as one of the factors.

Lin28 is an mRNA binding protein expressed in embryonic stem cells and embryonic carcinoma cells associated with differentiation and proliferation. Thomson et al. demonstrated it is a factor in iPS generation, although it is unnecessary.

Klf4 of the Klf family of genes was initially identified by Yamanaka et al. and confirmed by Jaenisch et al. as a factor for the generation of mouse iPS cells and was demonstrated by Yamanaka et al. as a factor for generation of human iPS cells. However, Thompson et al. reported that Klf4 was unnecessary for generation of human iPS cells and in fact failed to generate human iPS cells. Klf2 and Klf4 were found to be factors capable of generating iPS cells, and related genes Klf1 and Klf5 did as well, although with reduced efficiency.

The Myc family of genes are proto-oncogenes implicated in cancer. Yamanaka et al. and Jaenisch et al. demonstrated that C-myc is a factor implicated in the generation of mouse iPS cells and Yamanaka et al. demonstrated it was a factor implicated in the generation of human iPS cells. However, Thomson et al. and Yamanaka et al. reported that C-myc was unnecessary for generation of human iPS cells. Usage of the "Myc" family of genes in induction of iPS cells is troubling for the eventuality of iPS cells as clinical therapies, as 25% of mice transplanted with C-myc-induced iPS cells developed lethal teratomas. N-myc and L-myc have been identified to induce instead of C-myc with similar efficiency.

SV40 large antigen may be used to reduce or prevent the cytotoxcity which may occur when C-myc is expressed.

The reprogramming proteins used in the present invention can be substituted by protein homologs with about the same reprogramming functions. Nucleic acids encoding those homologs could also be used for reprogramming. Conservative amino acid substitutions are preferred—that is, for example, aspartic-glutamic as polar acidic amino acids; lysine/arginine/histidine as polar basic amino acids; leucine/isoleucine/methionine/valine/alanine/glycine/proline as non-polar or hydrophobic amino acids; serine/threonine as polar or uncharged hydrophilic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting polypeptide. Whether an amino acid change results in a functional polypeptide can readily be determined by assaying the specific activity of the polypeptide.

VIII. Selection and Differentiation of iPS Cells

In certain aspects of the invention, after reprogramming factors are introduced into hematopoietic progenitor cells, cells will be cultured as described above (optionally selected for the presence of vector elements like positive selection or screenable marker to concentrate transfected cells). Reprogramming vectors may express reprogramming factors in these cells and replicate and partition along with cell division. Alternatively, reprogramming proteins could enter these cells and their progeny by replenishing medium containing the reprogramming proteins. These reprogramming factors will reprogram the somatic cell genome to establish a self-sustaining pluripotent state, and over time after removal of positive selection for the presence of vectors, exogenous genetic elements will be lost gradually without the need to add supplemental reprogramming proteins.

These induced pluripotent stem cells could be selected from progeny derived from these peripheral blood cells based on embryonic stem cell characteristics because they are expected to be substantially identical to pluripotent embryonic stem cells. An additional negative selection step could be also employed to accelerate or help selection of iPS cells essentially free of exogenous genetic elements by testing the absence of reprogramming vector DNA or using selection markers, such as reporters.

A. Selection for Embryonic Stem Cell Characteristics

The successfully generated iPSCs from previous studies were remarkably similar to naturally-isolated pluripotent stem cells (such as mouse and human embryonic stem cells, mESCs and hESCs, respectively) in the following respects, thus confirming the identity, authenticity, and pluripotency of iPSCs to naturally-isolated pluripotent stem cells. Thus, induced pluripotent stem cells generated from the methods disclosed in this invention could be selected based on one or more of following embryonic stem cell characteristics.

i. Cellular Biological Properties

Morphology: iPSCs are morphologically similar to ESCs. Each cell may have round shape, dual nucleoli or large nucleolus and scant cytoplasm. Colonies of iPSCs could be also similar to that of ESCs. Human iPSCs form sharp-edged, flat, tightly-packed colonies similar to hESCs and mouse iPSCs form the colonies similar to mESCs, less flat and more aggregated colonies than that of hESCs.

Growth properties: Doubling time and mitotic activity are cornerstones of ESCs, as stem cells must self-renew as part of their definition. iPSCs could be mitotically active, actively self-renewing, proliferating, and dividing at a rate equal to ESCs.

Stem Cell Markers: iPSCs may express cell surface antigenic markers expressed on ESCs. Human iPSCs expressed the markers specific to hESC, including, but not limited to, SSEA-3, SSEA-4, TRA-1-60, TRA-1-81, TRA-2-49/6E, and Nanog. Mouse iPSCs expressed SSEA-1 but not SSEA-3 nor SSEA-4, similarly to mESCs.

Stem Cell Genes: iPSCs may express genes expressed in undifferentiated ESCs, including Oct4, Sox2, Nanog, GDF3, REX1, FGF4, ESG1, DPPA2, DPPA4, and hTERT.

Telomerase Activity: Telomerases are necessary to sustain cell division unrestricted by the Hayflick limit of ~50 cell divisions. hESCs express high telomerase activity to sustain self-renewal and proliferation, and iPSCs also demonstrate high telomerase activity and express hTERT (human telomerase reverse transcriptase), a necessary component in the telomerase protein complex.

Pluripotency: iPSCs will be capable of differentiation in a fashion similar to ESCs into fully differentiated tissues.

Neural Differentiation: iPSCs could be differentiated into neurons, expressing βIII-tubulin, tyrosine hydroxylase, AADC, DAT, ChAT, LMX1B, and MAP2. The presence of catecholamine-associated enzymes may indicate that iPSCs, like hESCs, may be differentiable into dopaminergic neurons. Stem cell-associated genes will be downregulated after differentiation.

Cardiac Differentiation: iPSCs could be differentiated into cardiomyocytes that spontaneously begin beating. Cardiomyocytes express cTnT, MEF2C, MYL2A, MYHCβ, and NKX2.5. Stem cell-associated genes will be downregulated after differentiation.

Teratoma Formation: iPSCs injected into immunodeficient mice may spontaneously form teratomas after certain time, such as nine weeks. Teratomas are tumors of multiple lineages containing tissue derived from the three germ layers endoderm, mesoderm and ectoderm; this is unlike other tumors, which typically are of only one cell type. Teratoma formation is a landmark test for pluripotency.

Embryoid Body: hESCs in culture spontaneously form ball-like embryo-like structures termed "embryoid bodies," which consist of a core of mitotically active and differentiating hESCs and a periphery of fully differentiated cells from all three germ layers. iPSCs may also form embryoid bodies and have peripheral differentiated cells.

Blastocyst Injection: hESCs naturally reside within the inner cell mass (embryoblast) of blastocysts, and in the embryoblast, differentiate into the embryo while the blastocyst's shell (trophoblast) differentiates into extraembryonic tissues. The hollow trophoblast is unable to form a living embryo, and thus it is necessary for the embryonic stem cells within the embryoblast to differentiate and form the embryo. iPSCs injected by micropipette into a trophoblast to generate a blastocyst transferred to recipient females, may result in chimeric living mouse pups: mice with iPSC derivatives incorporated all across their bodies with 10%-90 and chimerism.

ii. Epigenetic Reprogramming

Promoter Demethylation: Methylation is the transfer of a methyl group to a DNA base, typically the transfer of a methyl group to a cytosine molecule in a CpG site (adjacent cytosine/guanine sequence). Widespread methylation of a gene interferes with expression by preventing the activity of expression proteins or recruiting enzymes that interfere with expression. Thus, methylation of a gene effectively silences it by preventing transcription. Promoters of pluripotency-associated genes, including Oct4, Rex1, and Nanog, may be demethylated in iPSCs, showing their promoter activity and the active promotion and expression of pluripotency-associated genes in iPSCs.

Histone Demethylation: Histones are compacting proteins that are structurally localized to DNA sequences that can effect their activity through various chromatin-related modifications. H3 histones associated with Oct/4, Sox2, and Nanog may be demethylated to activate the expression of Oct4, Sox2, and Nanog.

B. Selection for Residue Free Feature

A reprogramming vector such as oriP-based vector in this invention could replicate extra-chromosomally and lose it presence in host cells after generations. However, an additional selection step for progeny cells essentially free of exogenous vector elements may facilitate this process. For example, a sample of progeny cell may be extracted to test the presence or loss of exogenous vector elements as known in the art (Leight and Sugden, 2001).

A reprogramming vector may further comprise a selection marker, more specifically, a negative selection marker, such as a gene encoding a thymidine kinase to select for progeny cells essentially free of such a selection marker. The human herpes simplex virus thymidine kinase type 1 gene (HSVtk) acts as a conditional lethal marker in mammalian cells. The HSVtk-encoded enzyme is able to phosphorylate certain nucleoside analogs (e.g., ganciclovir, an antiherpetic drug), thus converting them to toxic DNA replication inhibitors. An alternative or a complementary approach is to test the absence of exogenous genetic elements in progeny cells, using conventional methods, such as RT-PCR, PCR, FISH (Fluorescent in situ hybridization), gene array, or hybridization (e.g., Southern blot).

C. Differentiation of iPS Cells

Various approaches may be used with the present invention to differentiate iPS cells into cell lineages including, but not limited to, hematopoietic cells, myocytes (e.g., cardiomyocytes), neurons, fibroblasts and epidermal cells, and tissues or organs derived therefrom. Exemplary methods of hematopoietic differentiation of iPS cells may include, for example, methods disclosed by U.S. Application No. 61/088,054 and No. 61/156,304, both incorporated herein by reference in their entirety, or embryoid body (EB) based methods (Chadwick et al., 2003; Ng et al., 2005). Fibronectin differentiation methods may also be used for blood lineage differentiation, as exemplified in Wang et al., 2007. Exemplary methods of cardiac differentiation of iPS cells may include embryoid body (EB) methods (Zhang, et al., 2009), OP9 stroma cell methods (Narazaki, et al., 2008), or growth factor/chemical methods (see U.S. Patent Publn. 20080038820, 20080226558, 20080254003 and 20090047739, all incorporated herein by reference in their entirety).

IX. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Generation of iPS Cells from Hematopoietic Progenitor Cells

As illustrated in FIG. 1, normal, non-mobilized peripheral blood from patients was processed to collect PBMCs and purified to enrich for cells expressing CD34. Those cells were then seeded to allow for expansion and transfected within approximately 1 week of seeding. They were then allowed a one day post-transfection incubation period followed by a recovery period of approximately 1-2 days and transitioned to 100% reprogramming medium. As cells attached and loose colonies became evident, the medium was gradually transitioned to TESR2 to support the formation of iPS cells.

Human whole blood was collected in vacutainers (range of volumes to be included here from 1-50 ml)

PBMCs were separated from human whole blood and either frozen or immediately processed to isolate CD34 cells.

Antibodies directed against CD34 were applied to PBMCs processed from peripheral blood and separated manually or automatically.

Purity was determined by flow cytometry (Accuri; Ann Arbor, Mich. USA) to detect the percent of cells expressing CD34 and the more general marker, CD45, to detect all hematopoietic progenitors. The purity of separated fractions had ranged from 20-96% positive for CD34 expression.

Cells enriched for CD34 expression were either frozen or immediately incubated with DNAseI (20 U/ml) for 10 minutes at 37° C. This step ensures removal of DNA released when cells lyse from stresses facilitated by thawing, purification, etc and limits cell clumping. Cells were spun and the supernatant containing the DNAse was removed. Cells were then left to recover overnight.

CD34 Expressing Cells are Expandable Using Cytokine-Enriched Medium.

It was found in this Example that the cytokine-enriched medium alone is sufficient to expand the total cell number in at least 3 independent cases.

Cytokine-Enriched Medium:

300 ng/ml of each: thrombopoietin (TPO), Flt3, and stem cell factor (SCF). 100 ng/ml of Interleukin 6 (IL6) and 10 ng/ml Interleukin 3 (IL3). The basal medium consists of bovine serum albumin (BSA), recombinant human insulin, iron-saturated human transferrin, 2-mercaptoethanol, Iscove's MDM, and additional supplements (Defined as Matrix-free in FIGS. 2A-2C). In a preferred embodiment, the BSA may be completely omitted. Furthermore, fully defined components are utilized in this medium. Alternatively, StemSpan H3000 (Stem Cell Technologies, catalog number 9850) supplemented with the above detailed concentrations of animal-free TPO, Flt3, SCF, IL6 and IL3 can be utilized.

CD34 Expressing Cells are Expandable Using Cytokine-Enriched Medium Coupled with Fibronectin Fragments.

It was observed in this Example that CD34$^+$ cells can be further expanded in the presence of a recombinant human fragment of fibronectin. It is 574 amino acids (63 kDa) and contains a central cell-binding domain (type III repeat, 8, 9, 10), a high affinity heparin-binding domain II (type III repeat 12, 13, 14), and CS1 site within the alternatively spliced IIICS region of human fibronectin (available from RetroNectin®, Takara). The fibronectin fragments were mixed with PBS at 5 ug/ml and deposited on non-treated tissue culture plates (Defined as Notch– in FIGS. 2A-2C)

CD34 Expressing Cells are Expandable Using Cytokine-Enriched Medium Coupled with Fibronectin Fragments and Immobilized Engineered Notch-1 Ligand (Delta1$^{ext-IgG}$, DLL1).

Delaney et al. demonstrate expansion of CD34$^+$ cells of greater than 100-fold from cord blood using Notch-1 ligand (Delaney et al., 2010). It was found in this Example that CD34$^+$ cells derived from peripheral blood are also expandable in the presence of Notch-1 ligand using a similar approach. (Defined as Notch+ in FIGS. 2A-2C). The ligand is a human peptide representing the extracellular domain of recombinant delta-like protein 1 (DLL1; aa 1-545) fused at the C-terminus to the Fc portion of Immunoglobulin G.

Expansion of CD34$^+$ Cells without Matrix or Notch-1 Ligand.

Figure 2A:
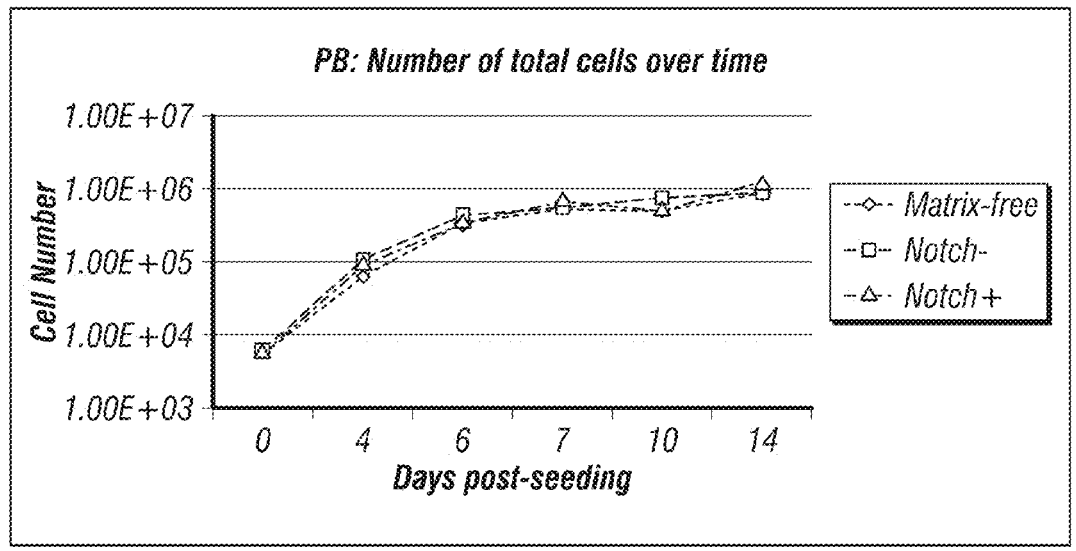
FIGS. 2A-2E—Hematopoietic progenitor cells (HPs) are expandable from non-mobilized blood donors.
Figure 2B:
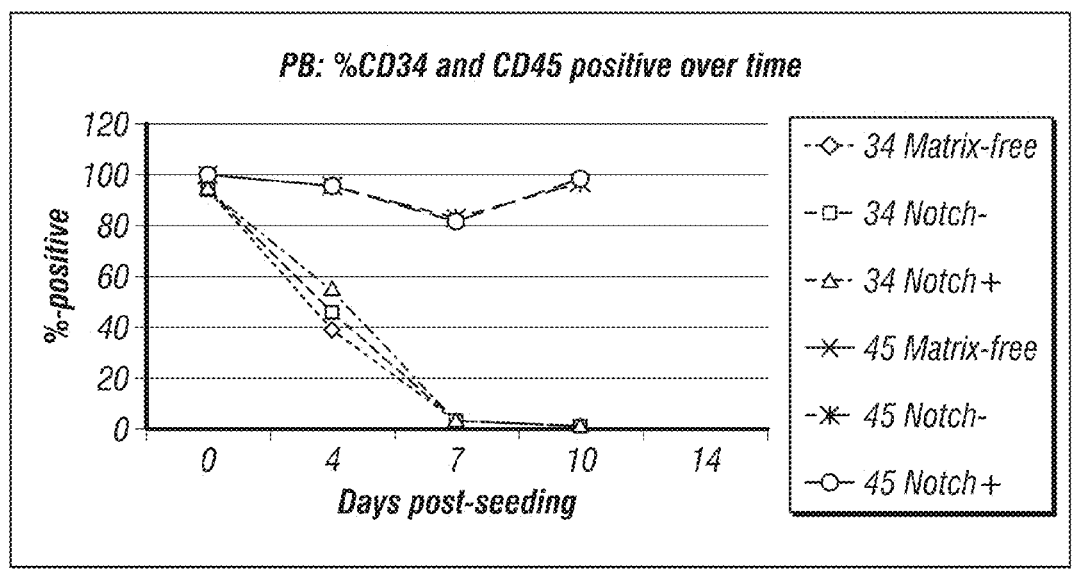
Figure 2C:
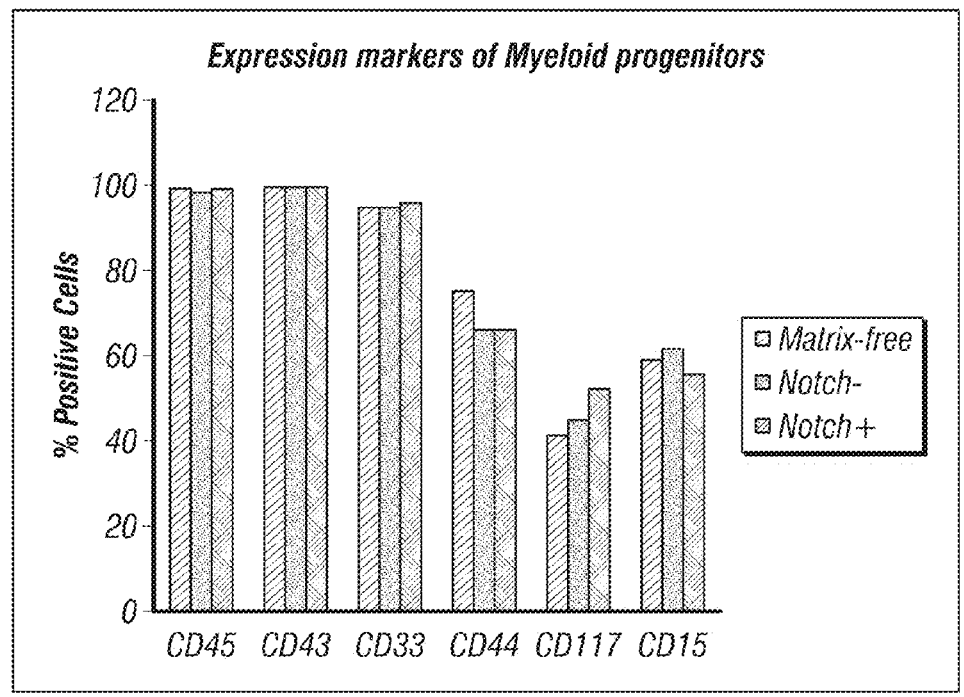
Figure 2D:
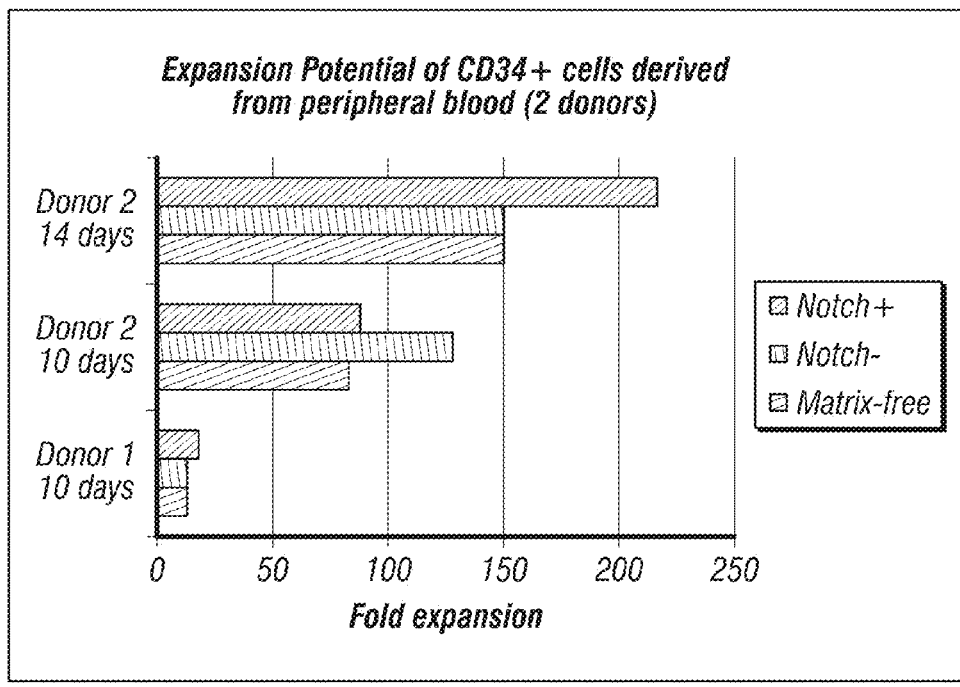
Figure 2E:
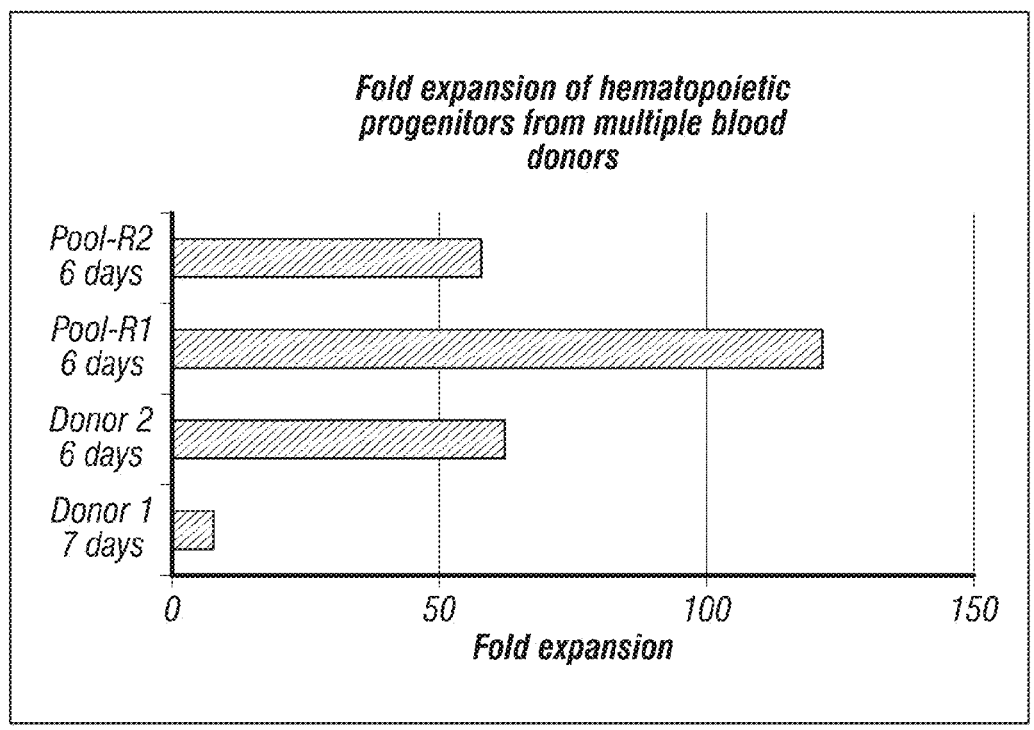

Essentially cells were seeded at $6 \times 10^3$ per well (24 well plates) or $1 \times 10^5$ per well (6 well plates), fed 4 days later, and transfected at 6 days post-expansion. FIGS. 2A-2C demonstrate fold expansion over time, rate of growth of the total population, and the natural decline of CD34 expression during that timeframe.

Figure 3:
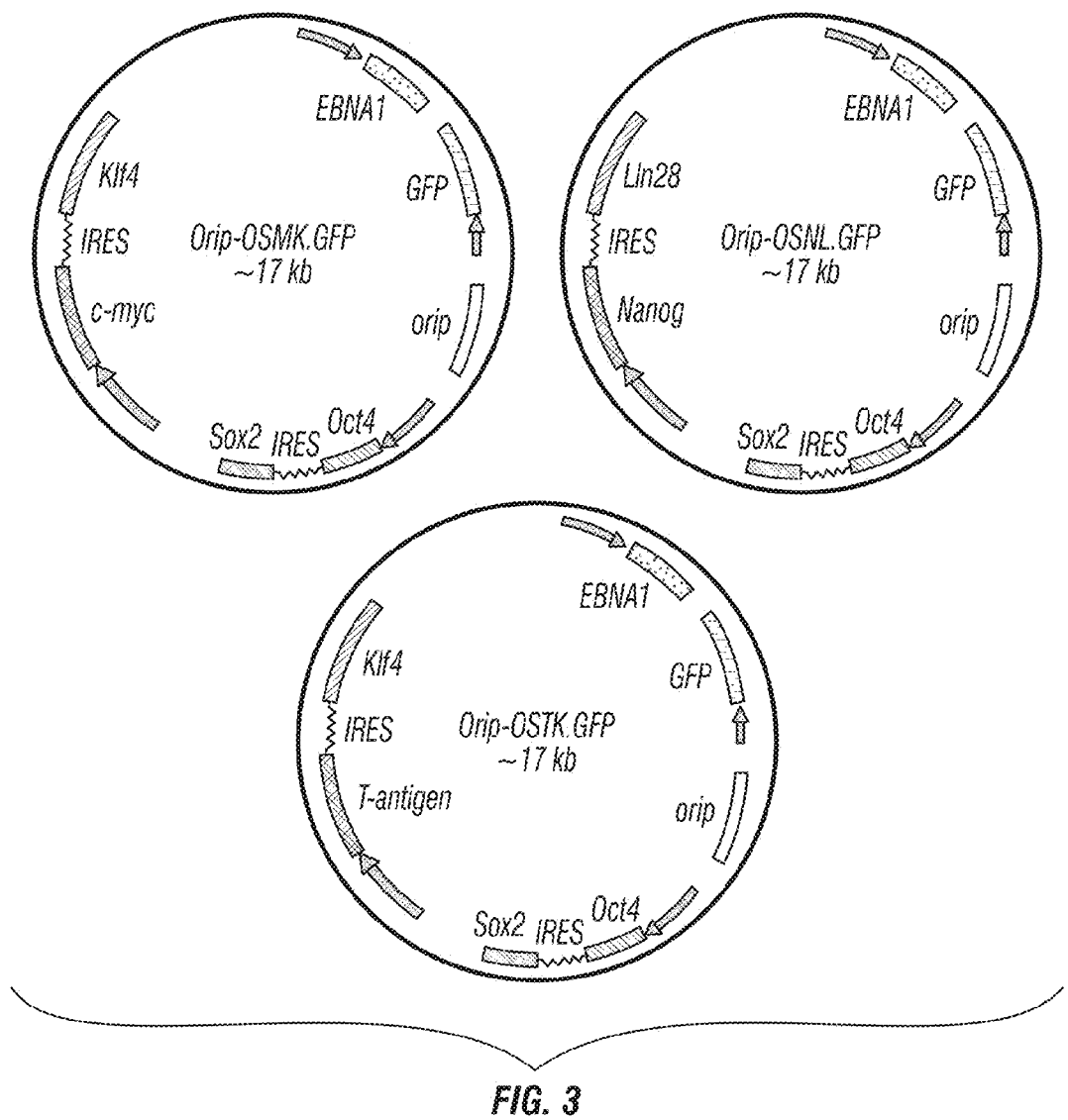
FIG. 3—Vectors for transfection of hematopoietic progenitors (HP)s. To successfully reprogram cells, HPs are transfected by electroporation with either a GFP-expressing control plasmid or a combination of plasmids expressing factors for reprogramming. There are multiple permutations of plasmids that can be used to express various combinations of reprogramming factors that have been used successfully and examples of such plasmids are shown herein. Each plasmid harbors oriP and the cassette expressing EBNA1 to ensure retention of the plasmids within transfected cells.

At day 6 post-expansion, cells are collected from the Matrix-free condition and transfected with a combination of plasmids containing the oriP-replicon. Reprogramming factors expressed from these plasmids may include any combination of the following: Oct4, Sox2, Nanog, Lin28, C-myc or L-myc, klf4, and SV40 Large T-antigen (FIG. 3). The Lonza Nucleofector device for single cuvette transfection or the 96 well shuttle version were used to transfect $2.5 \times 10^4$ to $1.5 \times 10^6$ cells. Table 1 below shows representative results following transfection using an oriP-based plasmid encoding eGFP on blood-derived hematopoietic progenitor cells, including CD34$^+$ cells. The table reflects results from a sample transfection using increasing numbers of input HPs expanded from peripheral blood. Cells were transfected with a control plasmid lacking the expression cassettes for the reprogramming factors. Transfection efficiency (% GFP+) was determined by calculating the percent of the population that does not stain positive for propidium iodide (PI).

TABLE 1

Transfection Results

| | Number of cells Transfected | | |
|---|---|---|---|
| | $5.5 \times 10^5$ | $7.5 \times 10^5$ | $1.2 \times 10^6$ |
| % GFP+ | 43 | 38 | 37 |
| % PI– | 21 | 22 | 27 |

Following transfection cells were resuspended in the same cytokine-rich medium used for expansion and incubated overnight for recovery. The following day cells were spun down and medium refreshed with cytokine-rich medium and recipient plates were prepared.

Recipient Reprogramming Plate Preparation.

24 hours post-transfection non-treated 6 well plates were coated with RetroNectin® (10 ug/well).

48 hours post-transfection plates were washed with PBS, blocked with 2% BSA, and washed again. Optionally, the 2% BSA blocking step may be omitted for animal-free culturing conditions. Transfected cells were brought to volume with reprogramming medium (Table 2) so that 2 ml of cells were seeded onto prepared recipient plates using a density ranging between $3 \times 10^4$ to $3 \times 10^5$ cells per well.

TABLE 2

Reprogramming Medium

| Components | Vendor | Final conc. |
|---|---|---|
| StemSpan | StemCellTechnologies | |
| N-2 supplement (100x) | Invitrogen | 1x |
| B-27 supplement (50x) | Invitrogen | 1x |
| NEAA (100x) | Invitrogen | 1x |
| Glutamax (100x) | Invitrogen | 0.5x |
| β-mercaptoethanol | Sigma | 1.7 μl |
| PD0325901 | StemGent | 0.5 μM |
| CHIR99021 | StemGent | 3 μM |
| A-83-01 | StemGente | 0.5 μM |
| HA-100 | StemGent | 10 μM |
| Zebrafish FGF | In-house | 100 ng/ml |

Feeding Reprogramming Cultures.

Cells are fed every other day. For the first feed, 2 ml of media are added to each well, and no medium is removed. For subsequent feeds, 2 ml are gently removed from each well and replaced with fresh media. Cells begin attaching 24 hours post-plating and loose colonies begin to form by 1 week. Cultures are transitioned to TESR2 (StemCell Technologies) without small molecules at approximately 7-10 days. This will represent a gradual shift since 2 ml of the previous medium will remain. If sufficient young colonies have formed, more media may be removed from wells so that a majority of the medium present is fresh. Round iPSC colonies surrounded by non-reprogrammed, differentiated cells emerged at approximately 20 days post-transfection. The cells surrounding the iPSC colonies represent blood cells that have adhered to the matrix or partially reprogrammed cells that have begun to differentiate. With the use of small molecule signaling inhibitors, actual iPSC colonies (Tra1-81 positive) were often nested within looser, non-iPSC areas or beneath more differentiated cells.

Example 2

Figure 4:
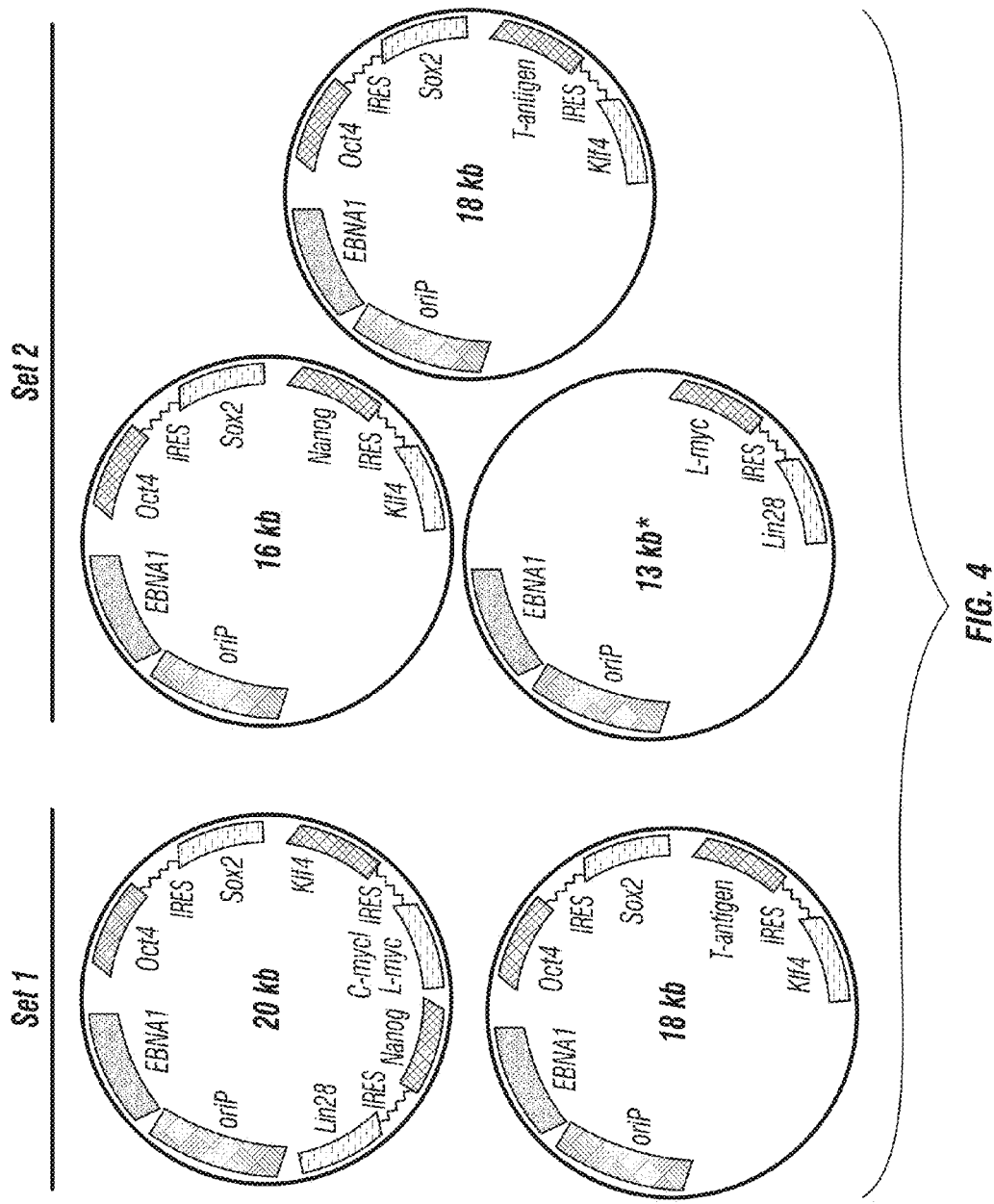
FIG. 4—Vector maps for polycistronic vectors—set 1 and set 2.

Optimization of Generation of iPS Cells from Hematopoietic Progenitor Cells Using Polycistronic Reprogramming Vectors Schematic maps of OriP-based reprogramming plasmids containing polycistronic messages are shown in FIG. 4 (Combination Set 1 and Set 2). Purified cells from PBMCs were expanded for 3 or 6 days. A range of input cell numbers were transfected with a control, oriP/EBNA1-based plasmid expressing GFP. The 3 and 6 day expanded PBMCs from donor GG were transfected with the reprogramming plasmids as described above.

Figure 5A:
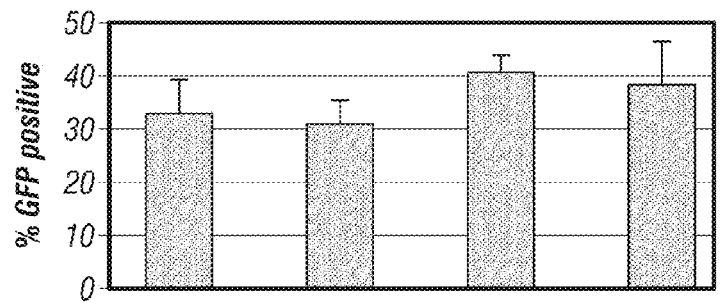
FIGS. 5A-5F—Optimizing input cell numbers and transfection efficiency for reprogramming.
Figure 5B:
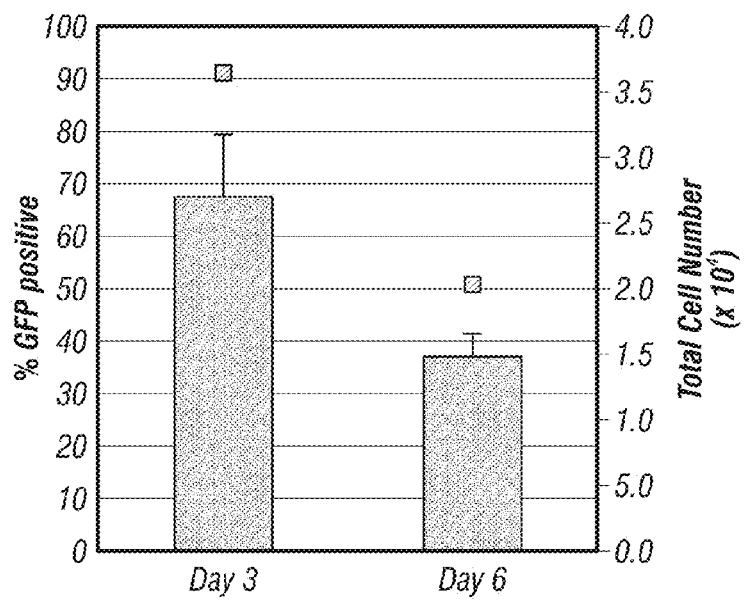
Figure 5C:
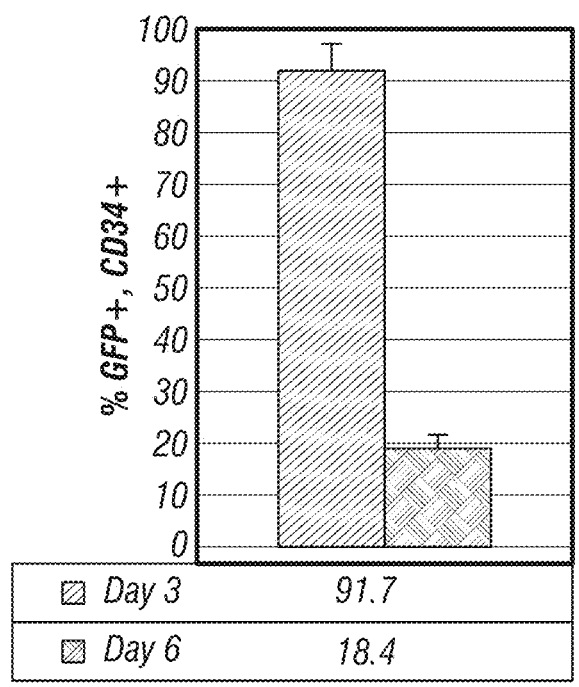

The transfection efficiency of lower numbers of CD34-enriched cells derived from PBMCs collected by leukophoresis was assessed by calculating the percentage of viable cells expressing GFP detected by flow cytometry. Viability was also determined by identifying the fraction of trypan blue-negative cells the day after transfection divided by the total number of input cells and was approximately 30% within a range of $1 \times 10^4$ to $1 \times 10^5$ input cells (data not shown). The efficiency of transfection was 30% when the input cell number ranged from $1 \times 10^4$ to $3 \times 10^4$ and roughly 40% when ranging from $6 \times 10^4$ to $1 \times 10^5$ cells (FIG. 5A). Purified cells from PBMCs were expanded for 3 or 6 days and $6 \times 10^4$ to $1 \times 10^5$ cells were transfected with the control, GFP-expressing plasmid. Transfection efficiency was two-fold higher when transfections were performed on cells expanded for 3 days rather than 6 days when the expression of CD34 was higher (FIG. 5B). Furthermore, over 90% of the day 3 transfected cells co-expressed GFP and CD34 while only 18% of the day 6 transfected population co-expressed both markers for (FIG. 5C). However, the 6 days of expansion did increase the overall number of cells for transfection. These results support the notion that the conditions selected for this protocol favor the transfection of CD34-expressing cells over other cell types in the population.

Figure 5D:
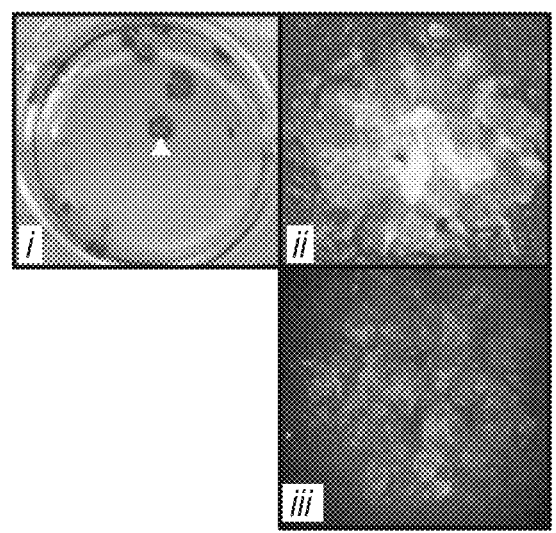

Recombinant protein fragments containing the active domains of human fibronectin (RetroNectin) or vitronectin consistently supported iPSC formation better than others tested. The efficiency of colony formation on RetroNectin-coated plates improved significantly when used in combination with StemSpan SFEM media, N2, B27, and a cocktail of small molecules that included PD0325901, CHIR99021, A-83-01, and HA-100 (FIG. 5D) A single well is shown from a 6 well plate that contains colonies staining positively for alkaline phosphatase activity (FIG. 5D, panel i). The white arrowhead highlights the colony magnified in panel ii that also stained positively for Tra1-81 expression, panel iii.

Figure 5E:
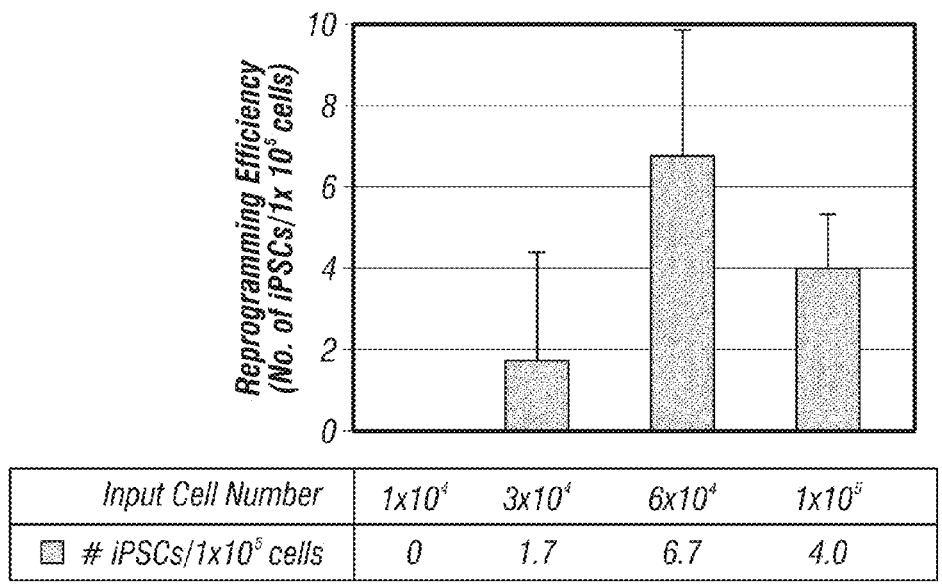

To optimize input cell numbers, reprogramming trials were performed using plasmid Set 2 on a range of input cell numbers expanded for 6 days (donor GG) (FIG. 5E).

Figure 5F:
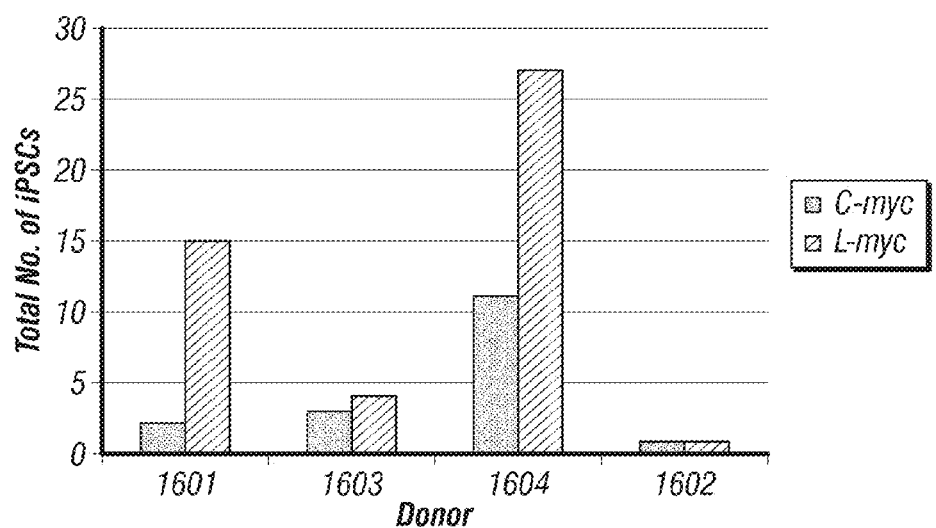

L-myc could be used instead of C-myc with potentially higher reprogramming efficiency. As shown in FIG. 5F, CD34-expressing cells purified from four different donors were expanded for 6 days and transfected using the plasmid combination that expresses C-myc (Set 1) or L-myc (Set 2) as a comparison and the total number of iPSCs resulting from each were compared.

Figure 6:
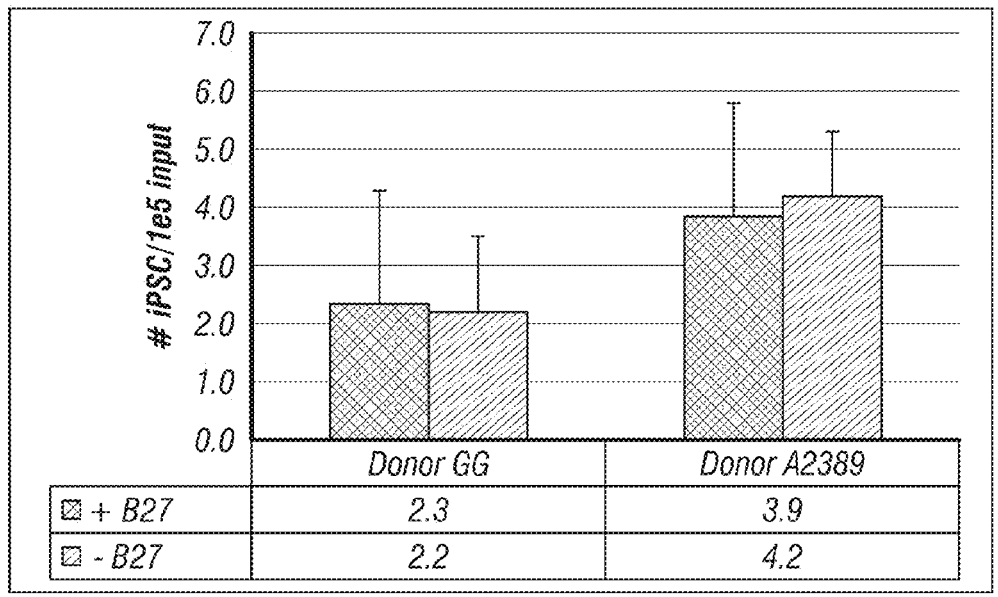
FIG. 6—Generation of iPSCs occurs in the absence of the BSA-containing supplement B27.

To achieve xeno-free culture without the need of animal component in B-27 supplement, it was demonstrated that the B-27 supplement could be omitted completely in the reprogramming medium as per FIG. 6.

Figure 7A:
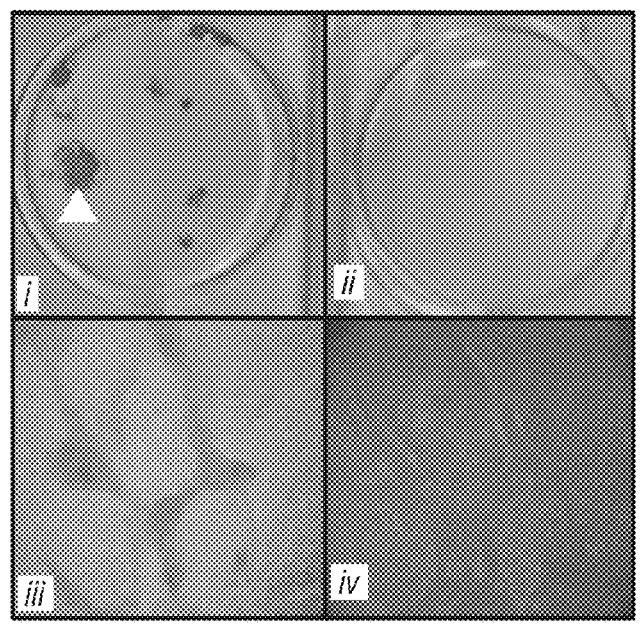
FIGS. 7A-7B—The amount of CD34-expression correlates with reprogramming efficiency.
Figure 7B:
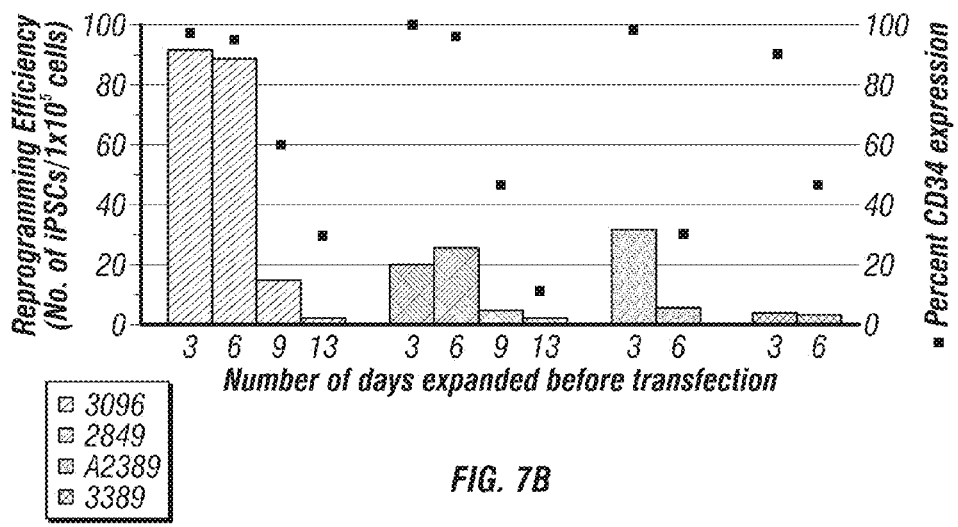

The amount of CD34-expression was shown to correlate with reprogramming efficiency (FIGS. 7A-7B). The isolation of CD34-expressing cells from PBMCs creates an additional step in the process; therefore, it was important to determine whether a correlation indeed existed between CD34-expression and reprogramming efficiency using the method detailed herein. The following set of experiments confirmed this correlation. First, host cell populations were deemed free of detectable levels of T, B, and NK cells at days 3 and 6 of expansion by flow cytometry using antibodies targeting CD3, CD19, and CD56 (n=9, data not shown). Second, the CD34-depleted population of cells consisting of 45% CD3, 10% CD19, 20% CD56 were unable to produce iPSCs using the feeder-free protocol herein (FIG. 7A, ii) as the counterparts purified for CD34-expression do in parallel (n=3, FIG. 7A, i). Third, CD34-expressing cells were purified from additional donors, transfected at different days of expansion coincident with reduced levels of CD34 expression and reprogrammed. The efficiency of reprogramming was lower as the percentage of CD34-expression decreased for all four donors (FIG. 7B). For example, donor 3096 exhibited over 90 iPSCs per $1\times10^5$ input cells when transfected after 3 days of expansion relative to 1 iPSC per $1\times10^5$ when expanded for 10 additional days when levels of CD34 expression are more than one-third lower. This result corroborates previous observations herein demonstrating higher transfection efficiencies at 3 days relative to 6 days of expansion where the percentage of CD34 is higher. In sum, these data support the notion that the amount of CD34-expression within a population of hematopoietic cells correlates with their ability to reprogram using feeder-free method detailed herein.

Figure 8A:
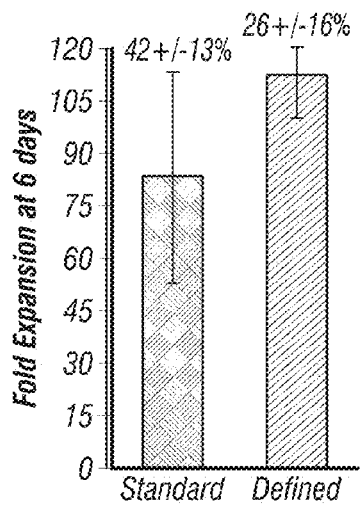
FIGS. 8A-8B—Blood cell-derived iPSCs using completely defined reagents (animal-free).
Figure 8B:

The fold expansion of CD34-expressing cells cultured under either standard or fully defined conditions is detailed in FIG. 8A. The ability to generate iPSCs using a completely defined method of reprogramming will further minimize variation and facilitate the production of clinical-grade iPSCs. A large pool of CD34-expressing cells was purified and mixed from multiple donors to ensure the number of cells required for multiple tests. Purified cells were successfully expanded in completely defined media at a magnitude of 113+/−11 fold compared to 83+/−32 fold for cells in standard conditions following 6 days of expansion. The absolute number of cells expressing CD34 is similar between the two populations when multiplied by the percentage of the population expressing CD34 bp flow cytometry despite the 30-fold difference between the two conditions. For example, 42+/−13% of the population expanded in standard conditions expressed CD34 and 26+/−16% expressed CD34 using completely defined conditions. The image in FIG. 8B represents one well of a 6 well plate containing colonies that stained positively for alkaline phosphatase following reprogramming of expanded cells enriched for CD34-expression with fully defined, animal-free reagents.

Multiple iPS clones were propagated from 26 donors using the methods herein detailed and a subset of the clones were selected for further characterization. The clones exhibited a normal karyotype and some were assessed at multiple passages to confirm their genetic integrity over time. The clones also expressed common cell surface markers Tra1-81 and SSEA-4 as determined by flow cytometry as well as endogenous genes indicative of pluripotency including DNT3B, REX1, TERT, UTF1, Oct4, Sox2, Nanog, Lin28, Klf4, and C-myc. Clones were also confirmed to be free of integrated and extrachromosomal plasmid DNA. The gradual loss of oriP-transfected plasmids was verified by collecting iPSCs at various passage numbers and screened by PCR with a limit of detection at 1 copy per cell and the loss was detectable within an average range of 7 to 10 passages. Interestingly, loss of oriP was evident at passages later than 10 when iPSCs were split with EDTA rather than dispase. Furthermore, there was also no amplification of gene segments indicative of immunoglobulin heavy chain (IgH) gene or T cell receptor rearrangements following analysis by PCR in the sample set of iPSCs tested. The lack of such rearrangements supports the claim that host cells originate from a hematopoietic precursor and that the protocol selectively favors the production of iPSCs from hematopoietic progenitors rather than more differentiated B or T cell types. Several iPSC clones from one donor were tested for competency to form neurons. Furthermore, five iPS clones from three different donors also formed teratomas after injection into immunodeficient (SCID) mice. Interestingly, the presence of residual transfected DNA did not appear to hinder the ability to form teratomas since clones from two donors did not lose plasmid DNA until passage 15 and 18 respectively after injection into mice for teratoma studies.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,714,680
U.S. Pat. No. 5,478,838
U.S. Pat. No. 5,728,581
U.S. Pat. No. 4,683,202
U.S. Pat. No. 4,684,611
U.S. Pat. No. 4,952,500
U.S. Pat. No. 5,302,523
U.S. Pat. No. 5,322,783
U.S. Pat. No. 5,384,253
U.S. Pat. No. 5,464,765
U.S. Pat. No. 5,538,877
U.S. Pat. No. 5,538,880
U.S. Pat. No. 5,550,318
U.S. Pat. No. 5,563,055
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,656,610
U.S. Pat. No. 5,702,932
U.S. Pat. No. 5,736,524
U.S. Pat. No. 5,780,448
U.S. Pat. No. 5,789,215
U.S. Pat. No. 5,925,565
U.S. Pat. No. 5,928,906
U.S. Pat. No. 5,935,819
U.S. Pat. No. 5,945,100
U.S. Pat. No. 5,981,274
U.S. Pat. No. 5,994,624
U.S. application Ser. No. 12/478,154
U.S. Appln. 61/058,858
U.S. Appln. 61/088,054
U.S. Appln. 61/156,304
U.S. Appln. 61/258,120
U.S. Publn. 20030211603
U.S. Publn. 20070238170
U.S. Publn. 20080038820
U.S. Publn. 20080226558
U.S. Publn. 20080254003
U.S. Publn. 20090047739
U.S. Publn. 2002/0076976
U.S. Publn. 2003/0059913
U.S. Publn. 2003/0087919
U.S. Publn. 2004/0002507
U.S. Publn. 2004/0002508
U.S. Publn. 2004/0014755
U.S. Publn. 2004/0039796
U.S. Publn. 2005/0192304
U.S. Publn. 2005/0209261
U.S. Publn. 2008/004287
U.S. Publn. 2007/0116680
Aasen and Belmonte, *Nat. Protoc.*, 5(2):371-382, 2010.
Abboud et al., *Blood*, 58:1148-1154, 1981.
Adams, *J. Virol.*, 61(5):1743-1746, 1987.
Aiyar et al., *EMBO J.*, 17(21):6394-6403, 1998.
Akkina et al., *J. Virol.*, 70(4):2581-2585, 1996.
Alexander et al., *Proc. Nat. Acad. Sci. USA*, 85:5092-5096, 1988.
Altmann et al., *Proc. Natl. Acad. Sci. USA*, 103(38):14188-14193, 2006.
Andrews et al., In: *Teratocarcinomas and Embryonic Stem Cells*, Robertson (Ed.), IRL Press, 207-246, 1987.
Aravind and Landsman, *Nucleic Acids* Res., 26(19):4413-4421, 1998.
Ausubel et al., Current Protocols in Molecular Biology, Greene Publishing Associates and Wiley Interscience, N.Y., 1994.
Baer et al., *Biochemistry*, 39:7041-7049, 2000.
Baer et al., *Nature*, 310(5974):207-211, 1984.
Bain et al., *Biochem. J.*, 408(3):297-315, 2007.
Bennett et al, *J. Biol. Chem.*, 277:34, 2002.
Bertrand et al., *J. Mol Biol.*, 333(2):393-407, 2003.
Bingham, *Cell*, 90(3):385-387, 1997.
Biswas et al., *Annals NY Acad. Sci.*, 590:582-583, 1990.
Biswas, et al., *J. Clin. Microbiol.*, 29:2228-2233, 1991.
Bochkarev et al., *Cell*, 84(5):791-800, 1996.
Bode et al., *Biol. Chem.*, 381:801-813, 2000.
Bode et al., *Gene Ther. Mol. Biol.*, 6:33-46, 2001.
Bode et al., *Science*, 255(5041):195-197, 1992.
Carbonelli et al., *FEMS Microbiol. Lett.*, 177(1):75-82, 1999.
Chadwick et al., *Blood*, 102(3):906-15, 2003.
Chandler et al., *Proc. Natl. Acad. Sci. USA*, 94(8):3596-601, 1997.
Chang, et al., *Frontiers in Bioscience*, 12:4393-4401, 2007.
Chaudhuri et al., *Proc. Natl. Acad. Sci. USA*, 98(18):10085-10089, 2001.
Chen and Okayama, *Mol. Cell. Biol.*, 7(8):2745-2752, 1987.
Chin et al., *Molecular Brain Res.*, 137(1-2):193-201, 2005.
Chow et al., *Cytometry Commun. Clinical Cytometry*, 46:72-78, 2001.
Christ et al., *Haematologica*, 92(9):1165-72, 2007.
Cocea, *Biotechniques*, 23(5):814-816, 1997.
DaCosta et al., *Molec. Pharmacol.*, 65(3):744-752, 2004.
Davies et al., *Biochem J.*, 351:95-105, 2000.
de Gouville et al., *Drug News Perspective*, 19(2):85-90, 2006.
deFelipe, *Prog. Brain Res.*, 136:215-38, 2002.
Delaney et al., *Nat. Med.*, 16(2):232-236, 2010.
Dhar et al., *Cell*, 106(3):287-296, 2001.
Downey et al., *J. Biol. Chem.*, 271(35):21005-21011, 1996.
Eliasson and Jonsson, *J. Cell Physiol.*, 222(1):17-22, 2010.
English et al., *Trends in Pharmac. Sci.*, 23(1):40-45, 2002.
Ercolani et al., *J. Biol. Chem.*, 263:15335-15341, 1988.
Ermakova et al., *J. Biol. Chem.*, 271(51):33009-33017, 1996.
Evans, et al., In: *Cancer Principles and Practice of Oncology*, Devita et al. (Eds.), Lippincot-Raven, N.Y., 1054-1087, 1997.
Fauser et al., *Stem Cells*, 1:73-80, 1981
Fechheimer et al., *Proc Natl. Acad. Sci. USA*, 84:8463-8467, 1987.
Fernandes et al., *Nature Cell Biology*, 6:1082-1093, 2004.
Fischer et al., *J. Virol.*, 71:5148-5146, 1997.
Fraley et al., *Proc. Natl. Acad. Sci. USA*, 76:3348-3352, 1979.
Frame et al, *Biochemical J.*, 359:1-16, 2001.

Frappier and O'Donnell, *Proc. Natl. Acad. Sci. USA,* 88(23): 10875-10879, 1991.
Gahn and Schildkraut, *Cell,* 58(3):527-535, 1989.
Gahn and Sugden, *J. Virol.,* 69(4):2633-2636, 1995.
Garrick et al., *Nat. Genet.,* 18:56-59, 1998.
Gellibert, et al., *J. Med. Chem.,* 49(7):2210-2221, 2006.
Ghosh and Bachhawat, In: *Liver Diseases, Targeted Diagnosis and Therapy Using Specific Receptors and Ligands,* Wu et al. (Eds.), Marcel Dekker, NY, 87-104, 1991.
Golde et al., *Proc. Natl. Acad. Sci. USA,* 77:593-596, 1980.
Gopal, *Mol. Cell. Biol.,* 5:1188-1190, 1985.
Gould et al, *Intl. J. Neuropsychopharmacology,* 7:387-390, 2004.
Gould et al, *Pharmacological Res.,* 48:49-53, 2003.
Graham and Van Der Eb, *Virology,* 52:456-467, 1973.
Harb et al., *PLoS One,* 3(8):e3001, 2008.
Harland and Weintraub, *J. Cell Biol.,* 101(3):1094-1099, 1985.
Haugland, In: *Molecular Probes: Handbook of Fluorescent Probes and Research Chemicals,* 1992-1994.
Hegde et al., *Nature,* 359(6395):505-512, 1992.
Hess et al., *Blood,* 104(6):1648-55, 2004.
Hung et al., *Proc. Natl. Acad. Sci. USA,* 98(4):1865-1870, 2001.
Inman et al., *Molec. Pharmacol.,* 62(1):65-74, 2002.
Jenke et al., *Proc. Natl. Acad. Sci. USA,* 101 (31), 11322-11327, 2004.
Julien et al., *Virology,* 326(2):317-328, 2004.
Kadaja-Saarepuu et al., *Oncogene,* 27(12):1705-1715, 2008.
Kaeppler et al., *Plant Cell Reports* 9: 415-418, 1990.
Kaminska et al., *Acta Biochimica Polonica,* 52(2):329-337, 2005.
Kanda et al., *Mol. Cell. Biol.,* 21(10):3576-3588, 2001.
Kaneda et al., *Science,* 243:375-378, 1989.
Karin et al. *Cell,* 36:371-379, 1989.
Kato et al, *J. Biol. Chem.,* 266:3361-3364, 1991.
Keller et al., *Curr. Opin. Cell Biol.,* 7(6):862-9, 1995.
Kennedy and Sugden, *Mol. Cell. Biol.,* 23(19):6901-6908, 2003.
Kennedy et al., *Proc. Natl. Acad. Sci. USA,* 100:14269-14274, 2003.
Kim et al., *J. Biol. Chem.,* 275(40):31245-31254, 2000.
Kim et al., *J. Virol.,* 66:3879-3882, 1992.
Kim et al., *Virology,* 239(2):340-351, 1997.
Kim et al., *Xenobiotica,* 38(3):325-339, 2008.
Kirchmaier and Sugden, *J. Virol.,* 69(2):1280-1283, 1995.
Kirchmaier and Sugden, *J. Virol.,* 72(6):4657-4666, 1998.
Klein et al, *Neoplasia,* 8:1-8, 2006.
Kleinman et al., *J. Biometer. Sci. Polymer Edn.,* 5:1-11, 1993.
Langle-Rouault et al., *J. Virol.,* 72(7):6181-6185, 1998.
Leight and Sugden, *Mol. Cell. Bio.,* 21:4149-61, 2001.
Levenson et al., *Hum. Gene Ther.,* 9(8):1233-1236, 1998.
Levitskaya et al., *Nature,* 375(6533):685-688, 1995.
Levitskaya et al., *Proc. Natl. Acad. Sci. USA,* 94(23):12616-12621, 1997.
Lindner and Sugden, *Plasmid,* 58:1-12, 2007.
Loh et al., *Blood,* 113(22):5476-5479, 2009.
Ludwig et al., *Nat. Biotechnol.,* 24(2):185-187, 2006b.
Ludwig et al., *Nat. Methods,* 3(8):637-46, 2006a.
Lusis, *Blood,* 57:13-21, 1981.
Macejak and Sarnow, *Nature,* 353:90-94, 1991.
Mackey and Sugden, *Mol. Cell. Biol.,* 19(5):3349-3359, 1999.
Mackey et al., *J. Virol.,* 69(10):6199-6208, 1995.
Maniatis, et al., *Molecular Cloning, A Laboratory Manual,* Cold Spring Harbor Press, Cold Spring Harbor, N.Y., 1988.
Manzini et al., *Proc. Natl. Acad. Sci. USA,* 103(47):17672-17677, 2006.
Marechal et al., *J. Virol.,* 73(5):4385-4392, 1999.
Martin, et al., *Nature Immunology,* 6:111-184, 2005.
Mattingly et al, *J. Pharmacol. Experimen. Therap.,* 316: 456-465, 2006.
Middleton and Sugden, *J. Virol.,* 66(1):489-495, 1992.
Nabel et al., *Science,* 244(4910):1342-1344, 1989.
Nanbo and Sugden, *EMBO J.,* 26:4252-62, 2007.
Narazaki, et al., *Circulation,* 118(5):498-506, 2008.
Ng et al., *Development,* 132(5):873-84, 2005.
Ng, *Nuc. Acid Res.,* 17:601-615, 1989.
Nicola, et al., *Blood,* 54:614-627, 1979.
Nicolau and Sene, *Biochim. Biophys. Acta,* 721:185-190, 1982.
Nicolau et al., *Methods Enzymol.,* 149:157-176, 1987.
Niller et al., *J. Biol. Chem.,* 270(21):12864-12868, 1995.
Noble et al, *Proc. Natl. Acad. Science,* USA, 102:6990-6995, 2005.
Okabe, *J. Cell. Phys.,* 110:43-49, 1982.
Omirulleh et al., *Plant Mol. Biol.,* 21(3):415-428, 1993.
PCT Appln. 2005/123902
PCT Appln. PCT/US94/08574
PCT Appln. PCT/US94/09760
PCT Appln. PCT/US94/10501
PCT Appln. WO 2003/062227
PCT Appln. WO 2007113505
PCT Appln. WO 2008/006583
PCT Appln. WO 2008/094597
PCT Appln. WO 2010/0003757
PCT Appln. WO 94/09699
PCT Appln. WO 95/06128
PCT Appln. WO 98/30679
PCT Appln. WO 99/20741
Pelletier and Sonenberg, *Nature,* 334(6180):320-325, 1988.
Piechaczek et al., *Nucleic Acids Res.,* 27(2):426-428, 1999.
Potrykus et al., *Mol. Gen. Genet.,* 199(2):169-177, 1985.
Potter et al., *Proc. Natl. Acad. Sci. USA,* 81:7161-7165, 1984.
Quitsche et al., *J. Biol. Chem.,* 264:9539-9545, 1989.
Rawlins et al., *Cell,* 42((3):859-868, 1985.
Reisman and Sugden, *Mol. Cell. Biol.,* 6(11):3838-3846, 1986.
Reisman et al., *Mol. Cell. Biol.,* 5(8):1822-1832, 1985.
Richards et al., *Cell,* 37:263-272, 1984.
Rinehart et al., *J. Clinical Oncol.,* 22:4456-4462, 2004.
Ring et al., *Diabetes,* 52:588-595, 2003.
Rippe, et al., *Mol. Cell. Biol.,* 10:689-695, 1990.
Ritzi et al., *J. Cell Sci.,* 116(Pt 19):3971-3984, 2003.
Ryan et al., *J. Gen. Virol.,* 78:(Pt 4):699-723, 1997.
Sambrook et al., In: *Molecular cloning: a laboratory manual,* $2^{nd}$ Ed., Cold Spring Harbor Laboratory Press, Cold Spring Harbor, N.Y., 1989.
Schaarschmidt et al., *EMBO J.,* 23(1):191-201, 2004.
Schaffer et al.; *Gene,* 302(1-2):73-81, 2003.
Schepers et al., *EMBO J.,* 20(16):4588-4602, 2001.
Scymczak et al., *Nat. Biotechnol.,* 22(5):589-94 2004.
Sears et al., *J. Virol.,* 77(21):11767-11780, 2003.
Sears et al., *J. Virol.,* 78(21):11487-11505, 2004.
Shire et al., *J. Virol.,* 73(4):2587-2595, 1999.
Su et al., *Proc. Natl. Acad. Sci. USA,* 88(23):10870-19874, 1991.
Sugden and Warren, *J. Virol.,* 63(6):2644-2649, 1989.

Sun et al., *Proc. Natl. Acad. Sci. USA,* 106(37):15720-15725, 2009.
Sutherland et al., *Exp. Hematol.,* 20:590, 1992.
Suzuki et al., *Cancer Res.,* 67(5):2351-2359, 2007.
Takahashi et al., *Cell,* 126(4):663-676, 2006.
Takahashi et al., *Cell,* 131:861, 2007.
Tojo, et al., *Cancer Science,* 96(11):791-800, 2005,
Tur-Kaspa et al., *Mol. Cell. Biol.,* 6:716-718, 1986.
Vodyanik et al., *Blood,* 108(6):2095-105, 2006.
Wagman, *Current Pharmaceutical Design,* 10:1105-1137, 2004.
Wang et al., *Mol. Cell. Biol.,* 26(3):1124-1134, 2006.
Wang et al., *Nat. Biotechnol.,* 25(3):317-8, 2007.
Watanabe et al., *Nat. Neurosci.,* 8(3):288-96, 2005.
Wilson et al., *Science,* 244:1344-1346, 1989.
Wong et al., *Gene,* 10:87-94, 1980.
Wrzesinski et al., *Clinical Cancer Res.,* 13(18):5262-5270, 2007.
Wu and Wu, *Biochemistry,* 27: 887-892, 1988.
Wu and Wu, *J. Biol. Chem.,* 262:4429-4432, 1987.
Wu et al., *J. Virol.,* 76(5):2480-2490, 2002.
Wysokenski and Yates, *J. Virol.,* 63(6):2657-2666, 1989.
Yates and Guan, *J. Virol.,* 65(1):483-488, 1991.
Yates et al., *J. Virol.,* 74(10):4512-4522, 2000.
Yates et al., *Nature,* 313:812-815, 1985.
Yates et al., *Proc. Natl. Acad. Sci. USA,* 81:3806-3810, 1984.
Yates, *Cancer Cells,* (6)197-205, 1988.
Ye et al., *Blood,* 114(27):5473-5480, 2009.
Yin et al., *Science,* 301(5638):1371-1374, 2003.
Ying, *Nature,* 453:519-23, 2008.
Yoshida et al., *Cell Stem Cell,* 5(3):237-41, 2009.
Yu et al., *Science,* 318:1917, 2007.
Yu et al., *Science,* 324:797, 2009.
Zhang et al., *Angew. Chem., Int. Ed.,* 48:2542-2545, 2009.
Zhang et al., *Bioorganic Med. Chem. Letters;* 10:2825-2828, 2000.
Zhou et al., *EMBO J.,* 24(7):1406-1417, 2005

What is claimed is:

1. A method for producing human induced pluripotent stem (iPS) cells from hematopoietic progenitor cells, the method comprising the steps of:
   a) providing a cell population of human peripheral blood cells from one or more subjects whose cells have not been mobilized with extrinsically applied granulocyte colony-stimulating factor (G-CSF) or granulocyte macrophage colony-stimulating factor (GM-CSF), the population comprising hematopoietic progenitor cells;
   b) culturing said population under feeder-free, defined expansion conditions to promote the expansion of said hematopoietic progenitor cells;
   c) introducing exogenous EBV-based episomal genetic elements into said expanded hematopoietic progenitor cells, wherein said episomal genetic elements replicate extra-chromosomally in said cells and express iPS reprogramming factors, further wherein the exogenous episomal genetic elements have one or more polycistronic cassettes.
   d) culturing said expanded hematopoietic progenitor cells in a media that is essentially free of feeder cells or feeder cell-conditioned medium, or in a xeno-free culture, thereby producing human iPS cells from said hematopoietic progenitor cells; and
   e) culturing said iPS cells sufficiently to remove episomal genetic elements.

2. The method of claim 1, wherein the cell population is comprised in a blood sample that is 1 to 10 ml in volume.

3. The method of claim 1, wherein the expansion conditions comprise an expansion medium comprising one or more cytokines including stem cell factor (SCF), Flt-3 ligand (Flt3L), thrombopoietin (TPO), Interleukin 3 (IL-3), or Interleukin 6 (IL-6).

4. The method of claim 3, wherein the expansion conditions do not comprise a Notch-1 ligand.

5. The method of claim 1, wherein the expansion conditions in step b) comprise a defined extracellular matrix.

6. The method of claim 1, wherein the expansion conditions in step b) does not comprise a matrix.

7. The method of claim 1, wherein the expansion conditions in step b) have or the culture in step d) has up to 7% oxygen tension.

8. The method of claim 1, wherein the reprogramming factors are Sox, Oct, Nanog, Lin-28, Klf4, C-myc (or L-myc), SV40 large T-antigen, or a combination thereof.

9. The method of claim 1, wherein the step c) occurs at about days 3, 4, 5 or 6 of the expansion step b).

10. The method of claim 1, wherein the starting number of the expanded hematopoietic progenitor cells in the step c) is from about $10^4$ to about $10^5$.

11. The method of claim 1, wherein the culture in step d) comprises a defined extracellular matrix.

12. The method of claim 11, wherein the defined extracellular matrix has a single type of extracellular matrix peptide.

13. The method of claim 12, wherein the defined extracellular matrix is a human fibronectin fragment.

14. The method of claim 1, wherein each of the steps are carried out in a chemically defined medium.

* * * * *

UNITED STATES PATENT AND TRADEMARK OFFICE
CERTIFICATE OF CORRECTION

| | | |
|---|---|---|
| PATENT NO. | : 9,447,382 B2 | Page 1 of 1 |
| APPLICATION NO. | : 14/179547 | |
| DATED | : September 20, 2016 | |
| INVENTOR(S) | : Mack | |

It is certified that error appears in the above-identified patent and that said Letters Patent is hereby corrected as shown below:

On the Title Page

Item (63), insert --Continuation of application No. 13/160,076, filed on Jun. 14, 2011, now Pat. No. 8,691,574.--.

Item (60), for filing date of 61/388,949, delete "Oct. 10, 2010" and insert --Oct. 1, 2010-- therefor.

Signed and Sealed this
Third Day of January, 2017

Michelle K. Lee
*Director of the United States Patent and Trademark Office*